United States Patent
Sattlegger et al.

(10) Patent No.: US 7,217,729 B2
(45) Date of Patent: May 15, 2007

(54) SUBSTITUTED INDOLES, PROCESS FOR THE PRODUCTION THEREOF AND USE THEREOF FOR COMBATTING PAIN

(75) Inventors: Michael Sattlegger, Bonn (DE); Helmut Buschmann, Esplugues de Llobregat (ES); Michael Przewosny, Aachen (DE); Werner Englberger, Stolberg (DE); Babette-Yvonne Koegel, Langerwehe-Hamich (DE); Hans Schick, Berlin (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 10/831,937

(22) Filed: Apr. 26, 2004

(65) Prior Publication Data

US 2004/0225003 A1 Nov. 11, 2004

Related U.S. Application Data

(63) Continuation of application No. PCT/EP02/11831, filed on Oct. 23, 2002.

(30) Foreign Application Priority Data

Oct. 29, 2001 (DE) .............................. 101 53 346

(51) Int. Cl.
*A61K 31/4045* (2006.01)
*A61K 31/404* (2006.01)
*A61K 31/4155* (2006.01)
*C07D 209/42* (2006.01)
*C07D 403/12* (2006.01)

(52) U.S. Cl. .................. 514/404; 514/419; 548/364.7; 548/492

(58) Field of Classification Search ................ 548/492, 548/364.7; 514/419, 404
See application file for complete search history.

(56) References Cited

U.S. PATENT DOCUMENTS

| | | | | |
|---|---|---|---|---|
| 3,041,344 A | 6/1962 | Jansen et al. | ................ | 260/294 |
| 4,113,866 A | 9/1978 | Lednicer | .................... | 424/248 |
| 5,145,845 A | 9/1992 | Johnson et al. | ............... | 514/80 |
| 5,922,752 A | 7/1999 | Harrison et al. | ............ | 514/419 |

FOREIGN PATENT DOCUMENTS

| | | |
|---|---|---|
| CH | 635 584 | 3/1977 |
| DE | 195 25 137 | 1/1997 |
| DE | 100 49 481 | 5/2002 |
| DE | 101 35 636 | 2/2003 |
| DE | 101 35 637 | 2/2003 |
| EP | 0 853 085 | 7/1998 |
| GB | 925429 | 5/1963 |
| GB | 1 501 475 | 2/1978 |
| WO | WO 95/10517 | 4/1995 |
| WO | WO 97/23216 | 7/1997 |
| WO | WO 200025770 A1 * | 5/2000 |
| WO | WO 01/47885 | 7/2001 |

OTHER PUBLICATIONS

* Indicates that the CAS Abstact and Structure are attached.*
"Sodium Cyanoborohydride—A Highly Selective Reducing Agent for Organic Functional Groups", C.F. Lane, Aldrich-Boranes, Inc., pp. 135-146, 1975.
"Fischer Indolization and Its Related Compounds. V.[1)] Indolization of Ethyl Pyruvate 2-Methoxyphenylhydrazone and Its N-Methyl Derivative with Protic Acids. Unpredictable Products and the Mechanism", Hisashi Ishh, et al., Chem. Pharm. Bull., vol. 21, No. 7, pp. 1481-1494, 1973.
Flick et al., "Untersuchungen zur chemischen struktur und analgetischen Wirkung von phenylsubstituierten Aminomethylcyclohexanolen", Arzneim-Forsch, Drug Res. 28 (I), 1978, pp. 107-113.
Salituro et al., "3-(2-Carboxyindol-3yl)propionic Acid-Based Antagonists of the N-Methyl-D-aspartic Acid Receptor Associated Glycine Binding Site", J. Med. Chem., 1992, 35, pp. 1791-1799.
Lalancette, et al., "Reductions of Functional Groups with Sulfurated Borohydrides. Application to Steroidal Ketones", Department de Chimie, Faculte des Sciences, Universite de Sherbrooke, Canada, pp. 526-532, Synthesis.
Lintz, et al., "Metabolismus von Tramadol bei Mensch und tier", Arzneim-Forsch/Drug Res. 31 (II), 1981, pp. 1932-1943.

(Continued)

*Primary Examiner*—Joseph K. McKane
*Assistant Examiner*—Jason M. Nolan
(74) *Attorney, Agent, or Firm*—Perman & Green, LLP

(57) ABSTRACT

Substituted indoles of the formula I,

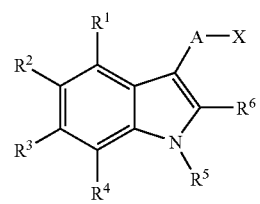

a process for the production of such compounds, pharmaceutical preparations containing these compounds and the use of these compounds for alleviating pain.

53 Claims, No Drawings

OTHER PUBLICATIONS

Di Fabio et al., "Substituted Indole-2-carboxylates as in Vivo Potent Antagonists Acting as the Strychnine-Insensitive Glycine Binding Site", J. Med. Chem., 40, 1997, pp. 841-860.

Gray et al., "Novel Indole-2-carboxylates as Ligands for the strychinine-Insensitive N-Methyl-D-asparatate-Linked Glycine Receptor", J. Med. Chem., 34, 1991, pp. 1283-1292.

Hart et al., Total Synthesis of (=)-Lythrancepine II and(=)-Lythrancepine III, J. Org. Chem., 52, 1987, pp. 4665-4673.

Borch et al., "Synthesis of 8-epi-Dendrobine", Journal of the American chemical Society, 1977, pp. 1612-1619.

Cram et al., "Host-Guest Complexation. 29. Expanded Hemispherands[1]", J. Am. Chem. Soc., 106, 1984, pp. 3286-3292.

Yoshihara, et al., "Conversion of Alcohols to Alkyl Halides using Iminium Salts", Department of Applied Chemistry, Faculty of Science and Engineering, Kinki University, Japan, 1980, pp. 746-748, Synthesis.

Suzuki, "Synthetic Studies via the cross-Coupling Reaction of Organoboron Derivatives with Organic Halides", Pure & Appl. Chem., vol. 63, No. 3, 1991, pp. 419-422.

Horner, et al., "Phosphinoxyde als Olefinierungsreagenzien", Aus dem Organisch-Chischen Institut der Universitat Mainz, 1959, pp. 2499-2505.

Mimura et al., "Synthesis and Evaluation of (Piperidinomethylene)bis(phosphonic acid) Derivatives as Anti-osteoporosis Agents", Chem. Pharm. Bull., 41 (11), 1993, pp. 1971-1986.

Schlosser, "The Stereochemistry of the Wittig Reaction", Organisch-Chemisches Institut der Universitat, Germany, pp. 1-30.

Gillois et al., "Diphenylbutadienes Syntheses by Means of the Wittig Reaction", Journal of Chemical Education, vol. 57, No. 2, 1980, pp. 161-162.

Escoda et al., "Alcoholes Terpenicos Monociclicos", Anales De Quimica, 1968, pp. 607-612.

El-Feraly et al., "Total Synthesis of Cannabispiran and (=)-Dehydrocannabispiran", Journal of Natural Products, vol. 44, No. 5, 1981, pp. 557-560.

Suzuki, "Organoboron Compounds in New Synthetic Reactions", Pure & Appl. Chem., vol. 57, No. 12, 1985, pp. 1749-1758.

Noller et al., "Isobutyl Bromide", Organic Syntheses, vol. 2, 1943, pp. 358-363.

Horner et al., "Reaktionen Mit triphenylphosphin-Dihalogeniden", Liebigs Ann Chem, vol. 626, 1959, pp. 26-35.

Suzuki, "New Synthetic Transformations Via Organoboron Compounds", Pure & Appl. Chem., vol. 66, No. 2, pp. 213-222, 1994.

Gribble et al., "Reactions of Sodium Borohydride in Acids Media. Selective Reduction of Aldehydes with Sodium Triacetoxyborohydride", J.C.S. Chem. Comm., 1975, pp. 535-536.

Bowman et al., "Quinoline Alkaloids. Part IX. A Partial Asymetric Synthesis of Orixine", J. Chem. Soc. 1967, pp. 2368-2371.

Vogel, "Physical Properties and Chemical Constitution. Part VIII. Alkyl Chlorides, Bromides, and Iodides", J. Chem. Soc. 1943, pp. 636-647.

Neville, et al., "Quinoline Alkaloids. Part 27. Synthesis of the Ptelea Alkaloids Pteflorine, Neohydroxylunine, O-Methylhydroxyluninium Salt and Hydroxylunine", J. Chem. Soc., 1991, 259-262.

Noller et al., "Synthesis of Dihydrochaulmoogric and Dihydrohydnocarpic Acids. II", Homologos of Dihydrochaulmoogric Acid, vol. 48, 1926, pp. 1080-1089.

Bendich, et al., "The Synthesis and Properties of 6-Chloropurine and Purine", Sloan-Kettering Division of Cornell University Medical College, 1954, pp. 6073-6077.

Danishefsky, et al., "A Stereospecific Route to Aziridinomitosanes: The Synthesis of Novel Mitomycin Congeners", J. A. Chem. Soc., 107, 1985, pp. 3891-3898.

Wilby et al., "Studies in Organophosphorus Chemistry. I. Conversion of Alcohols and Phenols to Halides by Tertiary Phosphine Dihalides", J. Am. Che. Soc. 46, 1924, pp. 964-965.

Lehmann, et al., "Uber die Tetrahydro-p-toluylsaure", Chem. Ber., vol. 68, 1935, pp. 1068-1072.

Arbusow, Pure & Applied Chemistry, vol. 9, 1964, pp. 307-335.

J. Chem. Soc., Apr. 20, 1954, pp. 2281-2282, vol. 76, Selwood et al.

Johnstone et al., "A Rapid, Simple, And Mild Procedure For Alkylation Of Phenols, Alcohols, Amides And Acids", Tetrahedron, vol. 35, pp. 2169-2173, 1979.

\* cited by examiner

SUBSTITUTED INDOLES, PROCESS FOR THE PRODUCTION THEREOF AND USE THEREOF FOR COMBATTING PAIN

This application is a continuation of PCT/EP02/11831, filed Oct. 23, 2002 and claims priority of German Patent Application 101 53346.2, filed Oct. 29, 2001.

The present invention relates to substituted indoles, to a process for the production thereof, to pharmaceutical preparations containing these compounds and to the use of these compounds for the production of pharmaceutical preparations.

The treatment of pain is of great medical significance.

There is a worldwide need for effective pain treatments.

The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain. However, they produce unwanted accompanying symptoms which include respiratory depression, vomiting, sedation, constipation and development of tolerance. Moreover, they are less effective in treating neuropathic or incidental pain, which is in particular frequently experienced by tumour patients.

The object of the present invention was accordingly to provide new compounds which are suitable as pharmaceutical active ingredients in pharmaceutical preparations, preferably as pharmaceutical active ingredients for combatting pain, preferably chronic or neuropathic pain and may be used for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, preferably hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

According to the invention, this object is achieved by the provision of substituted indole compounds of the general formula I below, optionally in the form of the diastereomers, pure enantiomers, racemates, non-racemic mixtures of enantiomers or diastereomers thereof and in each case optionally in the form of corresponding bases, salts and solvates, wherein these compounds exhibit in particular an excellent analgesic action.

The present invention therefore provides substituted indoles of the general formula I,

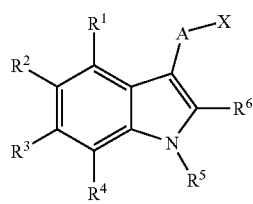

in which $R^1$, $R^2$, $R^3$ and $R^4$, identical or different, denote a linear or branched, saturated or unsaturated aliphatic $C_{1-10}$ residue or a saturated or unsaturated cycloaliphatic $C_{3-7}$ residue, wherein each of the above-stated residues may optionally be joined together via an ether bridge, or hydrogen, a halogen or a hydroxy group, $R^5$ denotes hydrogen, a linear or branched, saturated or unsaturated aliphatic $C_{1-10}$ residue, a saturated or unsaturated cycloaliphatic $C_{3-7}$ residue, an aryl or heteroaryl residue, wherein the aryl or heteroaryl residue may be optionally joined together via a $C_{1-6}$ alkylene group, a substituted sulfonyl residue or a group of the formula —$COR^7$, wherein $R^7$ has the meaning stated hereinafter, $R^6$ denotes a group of the formula —$COR^7$, a thiol group, a hydroxy group, a halogen, a cyano group, a nitro group or a group of the formula $SO_2CH_3$, $SO_2CF_3$ or $CF_3$, wherein the residue $R^7$ has the meaning stated hereinafter, $R^7$ denotes the group $OR^8$, $SR^8$, or $NR^8R^9$ denote, wherein the residues $R^8$ and $R^9$ have the meaning stated hereinafter, $R^8$ and $R^9$, identical or different, denote hydrogen, a linear or branched, saturated or unsaturated aliphatic $C_{1-10}$ residue, a saturated or unsaturated cycloaliphatic $C_{3-7}$ residue, an aryl- or heteroaryl residue or an aryl or heteroaryl residue attached via a $C_{1-6}$ alkylene group, A denotes a bridge with one of the following formulae: —$(CH_2)_{1-2}$—, —CH=CH—, —$(CH_2)_nCOO$—, —$(CH_2)_nCONH$—, —$(CH_2)_nO(CH_2)_pCO$—, —$(CH_2)_nO$—, —$(CH_2)_nNR^{1'}$—, in which n denotes 0, 1, 2 or 3 and p denotes 0 or 1, $R^{1'}$ has the meaning stated hereinafter and the bond to the residue X is always stated last and wherein bonding of the residues $X^{17}$ and $X^{18}$ is possible only via the three bridges stated first, and only a nitrogenous residue may be attached to the bridge of the formula —$CH_2$ via the nitrogen, and X denotes one of the following residues of the general formulae $X^1$ to $X^{19}$, in which the unoccupied bond line symbolises the bond to the bridge A and

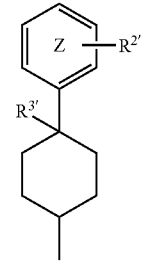

$X^1$

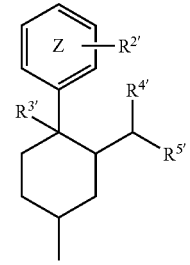

$X^2$

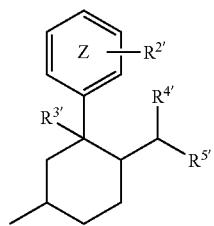 X³
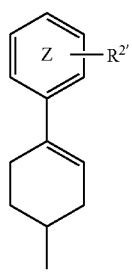 X⁴
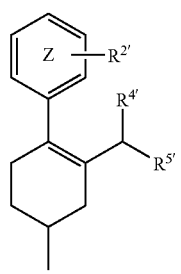 X⁵
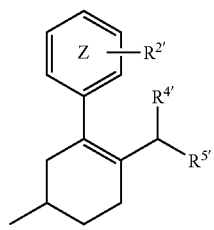 X⁶
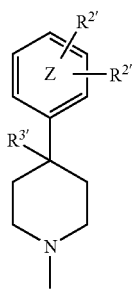 X⁷
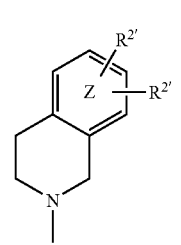 X⁸
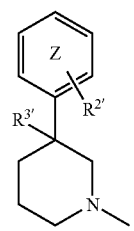 X⁹
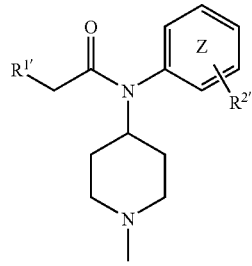 X¹⁰
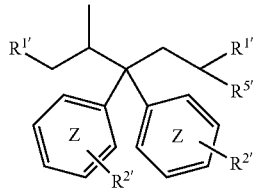 X¹¹
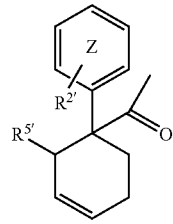 X¹²
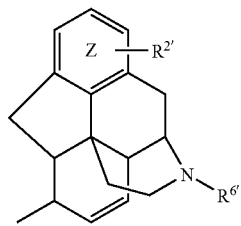 X¹³
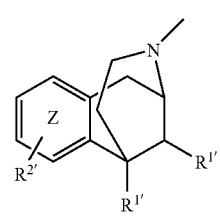 X¹⁴

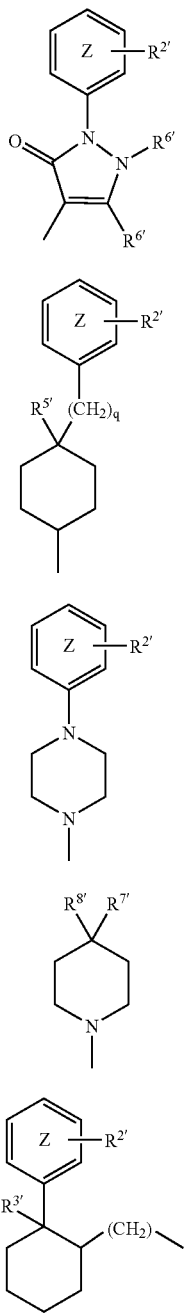

$R^{1'}$ denotes hydrogen, a linear or branched, saturated or unsaturated aliphatic $C_{1-10}$ residue, a saturated or unsaturated cycloaliphatic $C_{3-7}$ residue, an aryl or heteroaryl residue, $R^{2'}$ denotes a linear or branched, saturated or unsaturated aliphatic $C_{1-10}$ residue, a saturated or unsaturated cycloaliphatic $C_{3-7}$ residue or an aryl- or heteroaryl residue, wherein all the above-stated residues may optionally be joined via an ether, thioether or $SO_2$ bridge, or hydrogen, a halogen, a hydroxy, thiol, cyano or nitro group or a group of the formula $CH_2F$, $-CHF_2$, $-CF_3$ or $-NR^{1'}{}_2$ wherein the two residues $R^{1'}$ are identical or different and have the above-stated meaning, $R^{3'}$ denotes a linear or branched, saturated or unsaturated aliphatic $C_{1-10}$ residue, a saturated or unsaturated cycloaliphatic $C_{3-7}$ residue, an aryl or heteroaryl residue, wherein all the above-stated residues may optionally be joined via an ether or an ester bridge, hydrogen, a halogen, a hydroxy group, $R^{4'}$ denotes hydrogen, an aryl or heteroaryl residue, wherein the aryl or heteroaryl residue may comprise at least one substituent $R_{2'}$ with the above meaning, with the exception of hydrogen, $R^{5'}$ denotes a residue of the formula $-NR^{6'}{}_2$, wherein the two residues $R^{3'}$ may be identical or different and have the meaning stated hereinafter or may form a 3–7-membered ring together with the nitrogen atom connecting them as a ring member, which ring may optionally contain at least one oxygen and/or at least one further nitrogen as a ring atom, wherein the nitrogen may comprise a substituent $R^{10'}$ with the meaning stated hereinafter, $R^{6'}$ denotes a linear or branched, saturated or unsaturated aliphatic $C_{1-6}$ residue, a saturated or unsaturated cycloaliphatic $C_{3-7}$ residue, an aryl or heteroaryl residue, $R^{7'}$ denotes a cyano, amide or carboxylic acid residue, $R^{8'}$ denotes a residue of the formula $-NR^{9'}{}_2$, wherein the two residues $R^{9'}$ may be identical or different and have the meaning stated hereinafter or may form a 3–7-membered ring together with the nitrogen atom connecting them as a ring member, which ring may optionally contain at least one oxygen and/or at least one further nitrogen as a ring atom, $R^{9'}$ denotes hydrogen, a linear or branched aliphatic $C_{1-10}$ residue, $R^{10'}$ denotes hydrogen, a linear or branched, saturated or unsaturated aliphatic $C_{1-10}$ residue, an aryl or heteroaryl residue and Z denotes at least one optionally present oxygen, sulfur or nitrogen as a ring atom, and q denotes 0, 1, 2 or 3, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are preferred, in which $R^2$ denotes a linear or branched, saturated or unsaturated aliphatic $C_{1-3}$ residue or a halogen and $R^1$, $R^3$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are preferred, in which $R^3$ denotes a linear or branched, saturated or unsaturated aliphatic $C_{1-3}$ residue or a halogen and $R^1$, $R^2$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are preferred, in which $R^2$ and $R^3$, identical or different, denote a linear or branched, saturated or unsaturated aliphatic $C_{1-3}$ residue or a halogen and $R^1$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are preferred, in which $R^1$ and $R^3$, identical or different, denote a linear or branched, saturated or unsaturated aliphatic $C_{1-3}$ residue or a halogen and $R^2$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are particularly preferred, in which $R^2$ denotes a methyl residue or a chlorine and $R^1$, $R^3$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are particularly preferred, in which $R^3$ denotes a methyl residue or a chlorine and $R^1$, $R^2$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are particularly preferred, in which $R^1$ and $R^3$ in each case denote a methyl residue or a chlorine, $R^1$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are particularly preferred, in which $R^2$ and $R^3$ denote a methyl residue or a chlorine, $R^2$ and $R^4$ in each case denote hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

In addition, substituted indoles of the general formula I are preferred, in which the residue $R^7$ denotes the group $OR^8$ or $SR^8$, wherein the residue $R^8$ has the above-stated meaning, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are also preferred, in which $R^5$ denotes hydrogen, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are also preferred, in which $R^6$ denotes a group of the formula $COR^7$, wherein $R^7$ denotes the group $OR^8$ and the residue $R^3$ denotes hydrogen or a linear or branched, saturated or unsaturated aliphatic $C_{1-3}$ residue, preferably a methyl or ethyl group, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are also preferred, in which A denotes a bridge with one of the following formulae: —$CH_2$—, —$CH_2NR^{1'}$—, in which $R^{1'}$ denotes hydrogen or a linear or branched, saturated or unsaturated aliphatic $C_{1-3}$ group, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

Substituted indoles of the general formula I are also preferred, in which X denotes a residue of the following formula:

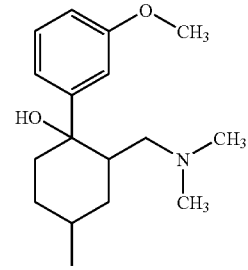

optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

The following substituted indoles are very particularly preferred:

5-Methyl-3-{[3'-(N,N-dimethylaminomethyl)-4'-hydroxy-4'-(3"-methoxyphenyl)-cyclohexylamino]-methyl}-1H-indole 2-carboxylic acid methyl ester, 4,6-Dimethyl-3-{[3'-(N,N-dimethylaminomethyl)-4'-hydroxy-4'-(3"-methoxyphenyl)-cyclohexylamino]-methyl}-1H-indole 2-carboxylic acid ethyl ester, 5-Chloro-3-{[3'-(N,N-dimethylaminomethyl)-4'-hydroxy-4'-(3"-methoxyphenyl)-cyclohexylamino]-methyl}-1H-indole 2-carboxylic acid ethyl ester, 4,6-Dichloro-3-{[3'-(N,N-dimethylaminomethyl)-4'-hydroxy-4'-(3"-methoxyphenyl)-cyclohexylamino]-methyl}-1H-indole 2-carboxylic acid ethyl ester, 4,6-Dimethyl-3-{[3'-(N,N-dimethylaminomethyl)-4'-hydroxy-4'-(3"-methoxyphenyl)-cyclohexyl-(N-methylamino)]-methyl}-1H-indole 2-carboxylic acid ethyl ester, 4,6-Dichloro-3-{[3'-(N,N-dimethylaminomethyl)-4'-hydroxy-4'-{3"-methoxyphenyl)-cyclohexyl-(N-methylamino)]-methyl}-1H-indole 2-carboxylic acid ethyl ester, 5-Chloro-3-{[3'-(N,N-dimethylaminomethyl)-4'-hydroxy-4'-(3"-methoxyphenyl)-cyclohexyl-(N-methylamino)]-methyl}-1H-indole 2-carboxylic acid ethyl ester, 4,6-Dichloro-3-[3'-hydroxy-3'-(3"-methoxyphenyl)-piperidin-1'-ylmethyl]-1H-indole 2-carboxylic acid ethyl ester, 4,6-Dimethyl-3-[3'-hydroxy-3'-(3"-methoxyphenyl)-piperidin-1'-ylmethyl]-1H-indole 2-carboxylic acid ethyl ester, 5-Methyl-3-[3'-hydroxy-3'-(3"-methoxyphenyl)-piperidin-1'-ylmethyl]-1H-indole 2-carboxylic acid ethyl ester, 5-Chloro-3-[3'-hydroxy-3'-(3"-methoxyphenyl)-piperidin-1'-ylmethyl]-1H-indole 2-carboxylic acid ethyl ester, 5-Methyl-3-{[3'-(N,N-dimethylaminomethyl)-4'-hydroxy-4'-(3"-methoxyphenyl)-cyclohexylamino]-methyl}-1H-indole 2-carboxylic acid, 5-Chloro-3-{[3'-(N,N-dimethylaminomethyl)-4'-hydroxy-4'-(3"-methoxyphenyl)-cyclohexylamino]-methyl}-1H-indole 2-carboxylic acid, 4,6-Dimethyl-3-{[3'-(N,N-dimethylaminomethyl)-4'-hydroxy-4'-(3"-methoxyphenyl)-cyclohexylamino]-methyl}-1H-indole 2-carboxylic acid, 4,6-Dichloro-3-{[3'-(N,N-dimethylaminomethyl)-4'-hydroxy-4'-(3"-methoxyphenyl)-cyclohexylamino]-methyl}-1H-indole 2-carboxylic acid, 4,6-Dichloro-3-[3'-hydroxy-3'-(3"-methoxyphenyl)-piperidin-1'-ylmethyl]-1H-indole 2-carboxylic acid, 5-Chloro-3-[3'-hydroxy-3'-(3"-methoxyphenyl)-piperidin-1'-ylmethyl]-1H-indole 2-carboxylic acid, 4,6-Dichloro-3-{[4'-hydroxy-4'-(3"-methoxyphenyl)-cyclohexylamino]-methyl}-1H-indole 2-carboxylic acid ethyl ester, 4,6-Dichloro-3-({[4'-hydroxy-4'-(3"-methoxyphenyl)-cyclohexyl]-(N-methylamino)}-methyl)-1H-indole 2-carboxylic acid ethyl ester, 4,6-Dichloro-3-({[2'-hydroxy-2'-(3"-methoxyphenyl)-cyclohexylmethyl]-amino}-methyl)-1H-indole 2-carboxylic acid ethyl ester, 5-Chloro-3-({[2'-hydroxy-2'-(3"-methoxyphenyl)-cyclohexylmethyl]-amino}-methyl)-1H-indole 2-carboxylic acid ethyl ester, 4,6-Dimethyl-3-({[2'-hydroxy-2'-(3"-methoxyphenyl)-cyclohexylmethyl]-amino}-methyl)-1H-indole 2-carboxylic acid ethyl ester, 5-Methyl-3-({[2'-hydroxy-2'-(3"-methoxyphenyl)-cyclohexylmethyl]-amino}-methyl)-1H-indole 2-carboxylic acid ethyl ester, 4,6-Dichloro-3-({[2'-hydroxy-2'-(3"-hydroxyphenyl)-cyclohexylmethyl]-amino}-methyl)-1H-indole 2-carboxylic acid ethyl ester, 5-Chloro-3-({[2'-hydroxy-2'-(3"-hydroxyphenyl)-cyclohexylmethyl]-amino}-methyl)-1H-indole 2-carboxylic acid ethyl ester, 4,6-Dimethyl-3-({[2'-hydroxy-2'-(3"-hydroxyphenyl)-cyclohexylmethyl]-amino}-methyl)-1H-indole 2-carboxylic acid ethyl ester, 5-Methyl-3-({[2'-hydroxy-2'-(3"-hydroxyphenyl)-cyclohexylmethyl]-amino}-methyl)-1H-indole 2-carboxylic acid ethyl ester, 4,6-Dichloro-3-({[2'-hydroxy-2'-(3"-methoxyphenyl)-cyclohexylmethyl]-amino}-methyl)-1H-indole 2-carboxylic acid, 5-Chloro-3-({[2'-hydroxy-2'-(3"-methoxyphenyl)-cyclohexylmethyl]-amino}-methyl)-1H-indole 2-carboxylic acid, 4,6-Dimethyl-3-({[2'-hydroxy-2'-(3"-methoxyphenyl)-cyclohexylmethyl]-amino}-methyl)-1H-indole 2-carboxylic acid, 5-Methyl-3-({[2'-hydroxy-2'-(3"-methoxyphenyl)-cyclohexylmethyl]-amino}-methyl)-1H-indole 2-carboxylic acid, 4,6-Dichloro-3-({[2'-hydroxy-2'-(3"-hydroxyphenyl)-cyclohexylmethyl]-amino}-methyl)-1H-indole 2-carboxylic acid, 5-Chloro-3-({[2'-hydroxy-2'-(3"-hydroxyphenyl)-cyclohexylmethyl]-amino}-methyl)-1H-indole 2-carboxylic acid, 4,6-Dichloro-3-[(1',5'-dimethyl-3'-oxo-2'-phenyl-2',3'-dihydro-1'H-pyrazol-4'-ylamino)-methyl]-1H-indole 2-carboxylic acid ethyl ester, 4,6-Dimethyl-3-[(1',5'-dimethyl-3'-oxo-2'-phenyl-2',3'-dihydro-1'H-pyrazol-4-ylamino)-methyl]-1H-indole 2-carboxylic acid ethyl ester, 4,6-Dichloro-3-[4'-(4"-chlorophenyl)-4'-hydroxypiperidin-1'-ylmethyl]-1H-indole 2-carboxylic acid ethyl ester, 4,6-Dimethyl-3-[4'-(4"-chlorophenyl)-4'-hydroxypiperidin-1'-ylmethyl]-1H-indole 2-carboxylic acid ethyl ester, 4,6-Dichloro-3-(6',7'-dimethoxy-3',4'-dihydro-1'H-isoquinolin-2'-ylmethyl)-1H-indole 2-carboxylic acid ethyl ester, 4,6-Dimethyl-3-(6',7'-dimethoxy-3',4'-dihydro-1'H-isoquinolin-2'-ylmethyl)-1H-indole 2-carboxylic acid ethyl ester, 4,6-Dichloro-3-[4'-(3"-methoxyphenyl)-piperazin-1'-ylmethyl]-1H-indole 2-carboxylic acid ethyl ester, 4,6-Dimethyl-3-[4'-(3"-methoxyphenyl)-piperazin-1'-ylmethyl]-1H-indole 2-carboxylic acid ethyl ester, 4,6-Dichloro-3-(4'-carbamoyl-[1",4']bipiperidin-1'-ylmethyl)-1H-indole 2-carboxylic acid ethyl ester, 4,6-Dichloro-3-{[(4'-benzyl-4'-(N,N-dimethylamino)-cyclohexyl)-(N-propylamino)]-methyl}-1H-indole 2-carboxylic acid ethyl ester, 4,6-Dichloro-3-[(1',5'-dimethyl-3'-oxo-2'-phenyl-2',3'-dihydro-1' H-pyrazol-4'-ylamino)-methyl]-1H-indole 2-carboxylic acid, 4,6-Dichloro-3-[4'-(4"-chlorophenyl)-4'-hydroxypiperidin-1'-ylmethyl]-1H-indole 2-carboxylic acid, 4,6-Dimethyl-3-[4'-(4"-chlorophenyl)-4'-hydroxypiperidin-1'-ylmethyl]-1H-indole 2-carboxylic acid, 4,6-Dichloro-3-[4'-(3"-methoxyphenyl)-piperazin-1'-ylmethyl]-1H-indole 2-carboxylic acid, 4,6-Dichloro-3-(6',7'-dimethoxy-3',4'-dihydro-1'H-isoquinolin-2'-ylmethyl)-1H-indole 2-carboxylic acid, 4,6-Dimethyl-3-(6',7'-dimethoxy-31,4'-dihydro-1'H-isoquinolin-2'-ylmethyl)-1H-indole 2-carboxylic acid, 4,6-Dichloro-3-[4'-(3"-methoxyphenyl)-piperazin-1'-ylmethyl]-1H-indole 2-carboxylic acid, 4,6-Dichloro-3-(4'-carbamoyl-[1",4']bipiperidin-1'-ylmethyl)-1H-indole 2-carboxylic acid, 1-tert-Butoxycarbonyl-4,6-dichloro-3-{[3'-N,N-dimethylaminomethyl)-4'-hydroxy-4'-(3"-methoxyphenyl)-cyclohexylamino]-methyl}-indole 2-carboxylic acid ethyl ester, 4,6-Dichloro-3-{[3'-(N,N-dimethylaminomethyl)-4'-hydroxy-4'-(3"-methoxyphenyl)-cyclohexylamino]-methyl}-1H-methyl-indole 2-carboxylic acid ethyl ester, 4,6-Dichloro-3-{[3'-(N,N-dimethylaminomethyl)-4'-hydroxy-4'-(3"-methoxyphenyl)-cyclohexylamino]-methyl}-1-benzyl-indole 2-carboxylic acid ethyl ester, 5-Chloro-3-{[3'-(N,N-dimethylaminomethyl)-4'-hydroxy-4'-(3"-methoxyphenyl)-cyclohexylamino]-methyl}-1-benzyl-indole 2-carboxylic acid ethyl ester, 4,6-Dimethyl-3-(4'-carbamoyl-[1",4']bipiperidin-1'-ylmethyl)-1H-indole 2-carboxylic acid, 4,6-Dichloro-3-(4'-phenyl-3',6'-dihydro-2'H-pyridin-1'-ylmethyl)-1H-indole 2-carboxylic acid ethyl ester, 4,6-Dichloro-3-(4'-phenyl-3',6'-dihydro-2'H-pyridin-1'-ylmethyl)-1H-indole 2-carboxylic acid, 4,6-Dichloro-3-[4'-(4"-chloro-3"-trifluoromethylphenyl)-4'-hydroxypiperidin-1'-ylmethyl]-1H-indole 2-carboxylic acid ethyl ester, 4,6-Dimethyl-3-[4'-(4"-chloro-3"-trifluoromethylphenyl)-4'-hydroxypiperidin-1'-ylmethyl]-1H-indole 2-carboxylic acid ethyl ester, 4,6-Dichloro-3-[4'-(4"-chloro-3"-trifluoromethylphenyl)-4'-hydroxypiperidin-1'-ylmethyl-1H-indole 2-carboxylic acid, 4,6-Dimethyl-3-[4'-(4"-chloro-3"-trifluoromethylphenyl)-4'-hydroxypiperidin-1'-ylmethyl]-1H-indole 2-carboxylic acid optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular the hydrates.

The present invention further provides a process for the production of substituted indoles of the above-stated general formula I or corresponding stereoisomers, characterised in that A) an indole of the formula Y—R$^x$ is optionally derivatised, in which R$^x$ denotes hydrogen or a group of the formula —(CH$_2$)$_n$COOR, —(CH$_2$)$_n$OH or —(CH$_2$)$_n$NR$^{1'}$H, in which n denotes 0, 1, 2 or 3 and R$^{1'}$ has the above-stated meaning and R denotes hydrogen or an alkyl group, preferably a methyl or ethyl group, and Y denotes a residue of the general formula Y, in which the unoccupied bond line symbolises the bond to the residue R$^x$

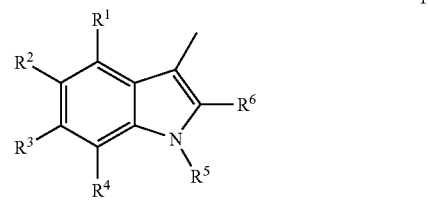

and in which R$^1$, R$^2$, R$^3$, R$^4$, R$^5$ and R$^6$ have the above-stated meaning, in that a) an indole of the formula Y—H is reacted with an N,N-disubstituted formamide, preferably N-methyl-N-phenylformamide, in the presence of phosphorus oxychloride in a suitable solvent, preferably 1,2-dichloroethane, to yield the corresponding aldehyde of the formula Y—CHO, b) an aldehyde of the formula Y—CHO according to step a) is reacted with the assistance of reducing agents, preferably sodium cyanoborohydride or NaBH$_2$S$_3$, in a suitable solvent, optionally in the presence of a buffer and with cooling to yield the corresponding alcohol of the formula Y—CH$_2$—OH, c) an alcohol of the formula Y—(CH$_2$)$_n$—OH according to step b) or D) is reacted with a brominating agent, preferably PBr$_3$ or Ph$_3$PBr$_2$ to yield the corresponding bromide of the formula Y—(CH$_2$)$_n$—Br, d) an ester of the formula Y—(CH$_2$)$_n$—COOR, in which R denotes an alkyl group, preferably a methyl or ethyl group, is saponified in the presence of a base, preferably sodium or potassium hydroxide, in a suitable solvent, preferably an alcohol/water mixture, particularly preferably in a methanol/ or ethanol/water mixture, to yield the corresponding carboxylic acid of the formula Y—(CH$_2$)N—COOH and is then worked up and the product is optionally purified, B) a compound of the formula X$^1$—R', in which X$^1$ has the above-stated meaning and R' denotes a functional group, is optionally produced in that a) 1,4-cyclohexanedione monoethylene ketal, 4-aminocyclohexan-1-one ethylene ketal or 4-oxocyclohexanecarboxylic acid is reacted with magnesium and a brominated or chlorinated, optionally substituted aromatic or heteroaromatic compound in a suitable solvent, preferably dry diethyl ether, at elevated temperature to yield the corresponding coupling product and then the ketal is optionally cleaved by reaction with hydrochloric acid in a suitable solvent, preferably tetrahydrofuran and is worked up, optionally followed by purification of the product of the formula X$^{1a}$═O, X$^{1a}$—NHR$^{1'}$ or X$^{1a}$—CO$_2$H, in which X$^{1a}$ denotes a residue of the formula X$^{1a}$ and R$^{1'}$, R$^{2'}$ and Z have the above-stated meaning and the unoccupied bond line symbolises the bond to the respective residue ═O, —NHR$^{1'}$ or —CO$_2$H,

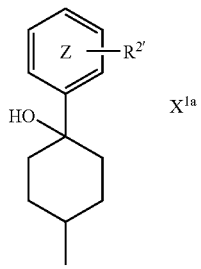

b) a ketone of the formula $X^{1a}$=O is optionally reacted in the presence of a suitable reducing agent, preferably sodium borohydride, in a suitable solvent, preferably methanol, to yield the corresponding alcohol of the formula $X^{1a}$—OH, is worked up and the product is optionally purified, c) a ketone of the formula $X^{1a}$=O is optionally reacted under protective gas, preferably nitrogen, in a suitable solvent, preferably tetrahydrofuran, firstly with ammonium trifluoroacetate and then with glacial acetic acid and sodium triacetoxyborohydride, to yield the corresponding amine of the formula $X^{1a}$—$NH_2$, is worked up and the product is optionally purified, d) a carboxylic acid of the formula $X^{1a}$—$CO_2H$ is optionally activated by reaction with dicyclohexylcarbodiimide or by conversion into the carboxylic acid chloride or a mixed anhydride, is reacted with diazomethane in a suitable solvent, preferably ether, and then treated with water, worked up and the product of the formula $X^{1a}$—CO—$CH_2$—OH is optionally purified, e) the hydroxy group in position 4 of the cyclohexane ring in the residue $X^{1a}$ is optionally converted into hydrogen, a halogen, an ether, ester, aryl or heteroaryl group or into an aliphatic or cycloaliphatic residue, in that α) in order to introduce an ether group, a compound from one of steps a)–d) is reacted with an aliphatic or cycloaliphatic residue in the presence of a suitable catalyst in a suitable solvent, preferably in the presence of sodium hydride in dimethylformamide or in the presence of potassium hydroxide in dimethyl sulfoxide, or with an alkylating agent in a suitable solvent, preferably with a diazo compound in diethyl ether, or with an aryl or heteroaryl compound in the presence of diethylazodicarboxylate and triphenylphosphine, β) in order to introduce a halogen, a compound from one of steps a)–d) is reacted with a halogenating agent in a suitable solvent, preferably with $POCl_8$ in dimethylformamide, with $PPh_3/Cl_2$, with $PPh_3/Br_2$, with triphenylphosphine/n-chlorosuccinimide or with $HCl/ZnCl_2$, γ) in order to introduce a hydrogen, a compound from step β) is reacted with hydrogen in the presence of a suitable catalyst, preferably palladium/carbon, in a suitable solvent, δ) in order to introduce an aliphatic or cycloaliphatic residue, an aryl or heteroaryl group, a compound from step β) is reacted with an aliphatic or cycloaliphatic boronic acid or a boronic acid ester or an aryl or heteroaryl borodihydroxide compound in the presence of palladium(II) acetate and potassium carbonate in a suitable solvent, preferably a dimethylformamide/water mixture, or ε) in order to introduce an ester group, a compound from one of steps a)–d) is reacted with a corresponding carboxylic acid chloride in the presence of a suitable catalyst in a suitable solvent and is then worked up, optionally followed by purification of the compound formed of the formula $X^1$—R', in which $X^1$ denotes the formula $X^1$

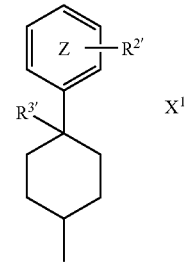

and R, $R^{2'}$ and $R^{3'}$ have the above-stated meaning,

C) a compound of the formula X—R', in which. X has the above-stated meaning and R' denotes a functional group, is optionally derivatised in that a) a ketone of the formula X=O is reacted 1) with methoxymethyl triphenylphosphinium chloride under protective gas in a suitable solvent, preferably in dimethylformamide, in the presence of sodium hydride and then with hydrochloric acid or 2) with $Me_3S^+BF_4^-$ to yield the corresponding aldehyde X—CHO extended by one carbon atom, b) an aldehyde of the formula X—CHO according to a) is reacted with a reducing agent, preferably sodium borohydride, in a suitable solvent, preferably an ethanol/water mixture, to yield the corresponding alcohol X—$CH_2$—OH, c) an alcohol X—$CH_2$—OH according to b) or of the formula X—OH is reacted with a brominating agent, preferably triphenylphosphine dibromide, in a suitable solvent, preferably acetonitrile, to yield the corresponding bromide of the formula X—$CH_2$—Br or X—Br, d) a bromide of the formula X—$CH_2$—Br according to c) is reacted with a phosphine of the formula $PR''_3$, in which R" denotes an organic residue, preferably a phenyl residue, in a suitable solvent, preferably toluene, ether, tetrahydrofuran or acetone, with cooling and under protective gas to yield the corresponding phosphonium salt $R''_3P^+$—$CHX^-$, e) a bromide of the formula X—$CH_2$—Br according to c) is reacted with a phosphite of the formula HP(O)$(OR''')_2$, in which R''' denotes an organic residue, at elevated temperature, preferably 200° C., to yield the corresponding phosphonate $(R'''O)_2P(O)$—$CH_2$—X and is then worked up and the product is optionally purified, D) a compound of the formula Y—$R^x$ or the derivative thereof from step A), in which Y has the above-stated meaning, is reacted with a compound of the formula $X^1$—R' or the derivative thereof from step B) or a compound of the formula X—R' or the derivative thereof from step C), in which X, $X^1$ and R' have the above-stated meaning, in that a) a carboxylic acid of the formula Y—(CH$_2$)$_n$—COOH is reacted with an amine of the formula X—NH$_2$ in the presence of a suitable condensing agent, preferably dicyclohexyl carbodiimide, 1-hydroxybenzotriazole and N-methylmorphine, in a suitable solvent, preferably dimethylformamide, with formation of an amide bridge, b) a carboxylic acid of the formula Y—(CH$_2$)$_n$—COOH is reacted with an alcohol of the formula X—OH in the presence of a suitable condensing agent in a suitable solvent with formation of an ester bridge, the reaction preferably taking place in the presence of methylimidazole and 1-(mesitylene-2'-sulfonyl)-3-nitro-1,2,4-triazole in tetrahydrofuran or in the presence of dicyclohexylcarbodiimide, 1-hydroxybenzotriazole and N-methylmorphine in dimethylformamide, c) a bromide of the formula Y—(CH$_2$)$_n$—Br is reacted with a compound of the formula X—CO(CH$_2$)$_p$—OH, in which p has the above-stated meaning, under protective gas in the presence of a suitable catalyst, preferably sodium hydride or potassium tert-butylate, in a suitable solvent, preferably dimethylformamide, with formation of a bridge of the formula —CO(CH$_2$)$_p$—O—(CH$_2$)$_n$—, d) an alcohol of the formula Y—(CH$_2$)$_n$—OH is reacted with a bromide of the formula X—Br under protective gas in the presence of a suitable condensing agent, preferably sodium hydride or potassium tert-butylate, in a suitable solvent, preferably dimethylformamide, with formation of an ether bridge, e) a bromide of the formula Y—(CH$_2$)$_n$—Br is reacted with an alcohol of the formula X—OH under protective gas in the presence of a suitable condensing agent, preferably sodium hydride or potassium tert-butylate, in a suitable solvent, preferably dimethylformamide, with formation of an ether bridge, f) an amine of the formula Y—(CH$_2$)$_n$—NHR$^{1'}$ is reacted with a bromide of the formula X—Br in the presence of a suitable catalyst, preferably caesium carbonate, in a suitable solvent, preferably dimethylformamide, with formation of an amino bridge, g) a bromide of the formula Y—(CH$_2$)$_n$—Br is reacted with an amine of the formula X—NHR$^1$ in the presence of a suitable catalyst, preferably caesium carbonate, in a suitable solvent, preferably dimethylformamide, with formation of an amino bridge, h) an aldehyde of the formula Y—CHO is reacted with an amine of the formula X—NHR$^{1'}$ in the presence of a suitable reducing agent, preferably sodium cyanoborohydride and sodium triacetoxyborohydride, in a suitable solvent, preferably a mixture of tetrahydrofuran and 1,2-dichloroethane, with formation of a —CH$_2$—NR$^{1'}$ bridge, i) an aldehyde of the formula Y—CHO is reacted with a phosphonium salt R"$_3$P$^+$—CHX$^-$, in which R" has the above-stated meaning, under protective gas in the presence of suitable catalysts in a suitable solvent, preferably in the presence of sodium methanolate in a mixture of hexane, diethyl ether and/or diisopropyl ether or in the presence of sodium hydride, potassium tert-butylate or a lithium amide in dimethylformamide or dimethyl sulfoxide, with formation of a —CH=CH— bridge or j) an aldehyde of the formula Y—CHO is reacted with a phosphonate of the formula (R'''O)$_2$P(O)—CH$_2$—X, in which R''' has the above-stated meaning, under protective gas in the presence of suitable catalysts, preferably sodium methanolate, sodium hydroxide, potassium hydroxide, sodium hydride, potassium tert-butylate or a lithium amide, in a suitable solvent, preferably dimethylformamide, dimethyl sulfoxide, diethyl ether, tetrahydrofuran, with formation of a —CH=CH— bridge, k) the —CH=CH— bridge from step i) or j) is optionally hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. with formation of a —CH$_2$—CH$_2$— bridge l) an aldehyde of the formula Y—CHO is reacted with a compound of the formula X—H, wherein X denotes a nitrogenous residue, in which the hydrogen is attached to the nitrogen, in the presence of a suitable catalyst, preferably sodium cyanoborohydride or sodium triacetoxyborohydride, in a suitable solvent, preferably 1,2-dichloroethane, with formation of a —CH$_2$— bridge and is then worked up and the product is optionally purified, E) an indole 2-carboxylic acid ester of the formula Y—A—X, in which Y, A and X have the above-stated meaning, wherein R$^6$ in Y denotes a group of the formula COR$^7$, in which R$^7$ denotes the group OR$^8$ and R$^8$ has the above-stated meaning with the exception of hydrogen, is optionally saponified in the presence of a base, preferably potassium or sodium hydroxide, in a suitable solvent, preferably an alcohol/water mixture, particularly preferably in a methanol/ or ethanol/water mixture and then worked up, followed optionally by purification of the indole 2-carboxylic acid of the formula Y—A—X, in which R$^6$ in Y denotes a group of the formula COR$^7$, in which R$^7$ denotes the group OR$^8$ and R$^8$ denotes hydrogen.

The solvents and reaction conditions used correspond to the solvents and reaction conditions conventional for these types of reactions.

The indoles of the formula Y—R$^x$ may be produced according to the Fischer Indole synthesis, which is known to the person skilled in the art from Gray et al., J. Med. Chem. 34, 1283 (1991); Iishii, Chem. Pharm. Bull. 21, 1481 (1973) and Salituro et al., J. Med. Chem. 35, 1791 (1992) and the literature cited therein.

Optionally, derivatisation reactions are necessary which introduce the functional groups for linking the indole skeleton to the residue X via the bridge A. The saponification of esters proceeds using conventional methods known to the person skilled in the art. The other reactions are known from the following literature and the literature cited therein; formylation from R. di Fabio et al., J. Med. Chem. 40, 841 (1997), international patent application WO 9510517 and U.S. Pat. No. 5,922,752, the reduction of aldehydes to alcohols from Synthesis 526 (1972) and Synthesis 135 (1975) and the reaction of alcohols to yield bromides from J. Am Chem. Soc. 48, 1080 (1926); J. Chem. Soc., 636 (1943); Org. Synth. Coll., Vol. 2, 358 (1943); Liebigs Ann. Chem. 626, 26 (1959); J. Am. Chem. Soc. 86, 964 (1964); J. Am. Chem. Soc. 99, 1612 (1977)

The starting compounds for the synthesis of compounds with the residue X$^1$, 1,4-cyclohexanedione monoethylene ketal, 4-oxocyclohexanecarboxylic acid and 4-aminocyclohexan-1-one ethylene ketal are known. 1,4-Cyclohexanedione monoethylene ketal and 4-oxocyclohexanecarboxylic acid are commercially obtainable or may be obtained using conventional methods known to the person skilled in the art. 4-Aminocyclohexan-1-one ethylene ketal is known from H.-J. Teuber, Liebigs. Ann. Chem., 781 (1990) and M. Mimura, Chem. Pharm. Bull., 41, 1971 (1993).

The reactions for synthesising compounds $X^1$—R' proceed according to conventional methods known to the person skilled in the art. The reaction of a cyclohexanone with a chlorinated or brominated, optionally substituted aromatic or heteroaromatic compound is known from Chem. Ber. 68, 1068 (1935), An. Quim. 64, 607 (1968) and Indian J. Biochem. 5, 79 (1968).

A modification or exchange of the hydroxy group in position 4 of the cyclohexane ring optionally takes place in the residue $X^1$. The reactions may be performed using conventional methods known to the person skilled in the art and are known from the following literature and the literature cited therein: alkylation of the hydroxy group from R. M. Bowman et al, Journal of the Chemical Society (C), 2368 (967); C. G. Neville et al, Journal of the Chemical Society, Perkin Trans, I, 259, (1991); F. Arnt et al, Chemische Berichte, 86, 951, (1953), Journal of Organic Chemistry, 52, 4665 (1987) and Tetrahedron 35, 2169 (1979), arylation or heteroarylation of the hydroxy group from Journal of the American Chemical Society 107, 3891 (1985), the introduction of a halogen from Journal of the American Chemical Society, 76, 6073 (1954) and Journal of the American Chemical Society, 86, 964 (1964), Journal of the Chemical Society, 636 (1943), Journal of the American Chemical Society, 106, 3286 (1984), Journal of the Chemical Society, 2281 (1954) and Synthesis, 746 (1980), the introduction of an alkyl, aryl or heteroaryl residue from A. Suzuki, Acc. Chem. Res., 15, 178 (1982); A. Suzuki, Pure Appl. Chem., 57, 1749 (1985); A. Suzuki, Pure Appl. Chem., 63, 419 (1991), A. Suzuki, Pure Appl. Chem., 66, 213 (1994), the conversion of chlorides to alkanes from Journal of Organic Chemistry, 23, 1938 (1958), esterification of the hydroxy group from W. König, R. Geiger, Chem. Ber. 103, 788 (1970).

Compounds with residues which are among the general residues $X^2$–$X^{19}$ are known from the following literature: $X^2$ and $X^5$ from German patent application P 3217639, $X^4$ from D. Lednicer, J. Med. Chem., 15, 1235 (1972), $X^3$ and $X^6$ from German patent application P 19525137, $X^7$ and $X^{10}$–$X^{14}$ from E. Friderichs, T. Christoph, H. Buschmann; Analgesics and Antipyretics; in: J. E. Bailey (Ed.); Ullmann's Encyclopedia of Industrial Chemistry, 6. Edition, Wyley VCH, Weinheim and A. F. Casy, R. T. Parfitt; Opioid Analgesics, Plenum Press, New York, $X^8$ from Forsyth, J. Chem. Soc., 127, 1666 (1925) and P. A. Grieco, J. Org. Chem., 55, 2271 (1990), $X^9$ from Shui, Synth. Commun., 27, 175 (1997), Balsamo, Chim. Ind. (Milan), 58, 519 (1976), Iselin, Helv. Chim. Acta, 37, 178 (1954), $X^{16}$ from German patent applications P 101356366 and P 101356374, $X^7$ from S.-H. Zkao, Tetrahedron Letters, 37, 4463 (1996); M. Nishiyama, Tetrahedron Letters, 39, 617 (1998); Jain, J. Med. Chem., 10, 812 (1967), $X^{18}$ from U.S. Pat. No. 3,041,344 and van de Westeringh, J. Med, Chem., 7, 619 (1964) and $X^{19}$ from Flick, Arzneimittel Forsch., 28, 107 (1978) and W. Lintz, Arzneimittel Forsch., 31, 1932 (1981). $X^{15}$ is known as metamizole in the literature and is commercially obtainable.

Compounds X—OH, X—NHR¹', X═O and X—CO(CH$_2$)$_p$OH are known from the literature or may be produced from known commercially obtainable compounds using conventional methods known to the person skilled in the art or using methods, such as are described in German patent application P100494811.

Derivatisation reactions are optionally required which introduce the functional groups for linking the residue X with the indole skeleton via the bridge A. These reactions may proceed using conventional methods known to the person skilled in the art and are known from the following literature and the literature cited therein: the reaction of ketones to yield aldehydes extended by one carbon from German patent application P 100494811; J. Nat. Prod., 44, 557 (1981) and Synth. Commun. 12, 613 (1982), the reduction of aldehydes to yield alcohols from German patent application P 100494811 and Chem. Commun. 535 (1975), the reaction of alcohols to yield bromides from J. Am Chem. Soc. 48, 1080 (1926); J. Chem. Soc., 636 (1943); Org. Synth. Coil, Vol. 2, 358 (1943); Liebigs Ann, Chem, 626, 26 (1959); J. Am. Chem. Soc. 86, 964 (1964); J. Am. Chem. Soc. 99, 1612 (1977), preparation of phosphonates and phosphonium salts is known from M. Schlosser, Top. Stereochem. 5, 1, (1970); R. Broos, D. Tavernier, M. Anteunis, J. Chem. Educ, 55, 813 (1978); G. Wittig, Angew. Chem. 92, 671 (1980); H. J. Bestmann; Pure Appl. Chem. 52, 771 (1980) and L. Horner, H. Hoffmann, H. G. Wippel, G. Klahre; Chem. Ber. 92, 2499 (1959); J. Gillois, G. Guillerm, M. Savignac, E. Stephan, L. Vo Quang, J. Chem. Educ. 57, 161 (1980); B. A. Arbusov; Pure Appl. Chem. 9, 307 (1964); A. K. Bhattacharya, G. Thyagarajan; Chem. Rev. 81, 415 (1981).

Linkage of the residue X with the indole skeleton via the bridge A may proceed using conventional methods known to the person skilled in the art and is known from the following literature and the literature in each case cited therein: the reaction of carboxylic acids with alcohols or amines in the presence of dicyclohexylcarbodiimide from W. König, R. Geiger, Chem. Ber. 103, 788 (1970), the reaction of carboxylic acids with alcohols in the presence of 1-(mesitylene-2'-sulfonyl)-3-nitro-1,2,4-triazole from Tetrahedron 36, 3075 (1980), etherification from Tetrahedron 35, 2169 (1979), Tetrahedron Lett. (1973), 21; Synthesis, 434 (1974); J. Org. Chem. 52, 4665 (1987); reductive amination from Org. React 3, 174 (1948); J. Am. Chem. Soc. 91, 3996 (1969); Org. Prep. Proced. Int. 11, 201 (1979); Org. Prep. Proced. Int. 17, 317 (1985), the Wittig or Wittig-Horner-Emmons reaction from G. Wittig, Angew. Chem. 92, 671, 1980; H. J. Bestmann; Pure Appl. Chem. 52, 771 (1980) and L. Horner, H. Hoffmann, H. G. Wippel, G. Klahre; Chem. Ber., 92, 2499 (1959); J. Gillois, G. Guillerm, M. Savignac, E. Stephan, L. Vo Quang; J. Chem. Educ. 57, 161 (1980); B. A. Arbusov; Pure Appl. Chem. 9, 307, 1964; A. K. Bhattacharya, G. Thyagarajan; Chem. Rev. (81) 415 (1981) and hydrogenation from Synthesis (1978), 329; J. Org. Chem. 34, 3684 (1969); J. Am. Chem. Soc. 91, 2579 (1969).

The corresponding literature descriptions are hereby introduced as a reference and are deemed to be part of the disclosure.

The substituted indole compounds according to the invention of the general formula I and corresponding stereoisomers may be isolated both in the form of the free bases thereof and in the form of corresponding salts.

The free bases of the respective compounds according to the invention of the general formula I and corresponding stereoisomers may be converted into the corresponding physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the respective compounds according to the invention of the general formula I and corresponding stereoisomers may preferably be converted into the corresponding hydrochlorides by combining the compounds according to the invention of the general formula I or corresponding stereoisomers as free bases dissolved in a suitable organic solvent, such as for example butane-2-one (methyl ethyl ketone), with trimethylsilyl chloride (TMSCl).

The free bases of the respective compounds according to the invention of the general formula I and corresponding stereoisomers may be converted into the corresponding physiologically acceptable salts with the free acid or a salt of a sugar substitute, such as for example saccharin, cyclamate or acesulfame.

The substituted indole compounds according to the invention of the general formula I and corresponding stereoisomers may optionally, like the corresponding acids, the corresponding bases or salts of these compounds, also be obtained in the form of the solvates thereof, preferably the hydrates thereof.

If the substituted indole compounds according to the invention of the general formula I are obtained by the production process according to the invention in the form of stereoisomers, preferably in the form of the racemates thereof or other mixtures of their various enantiomers and/or diastereomers, these may be separated and optionally isolated by conventional processes known to the person skilled in the art. Examples are chromatographic separation processes, in particular liquid chromatography processes at standard pressure or at elevated pressure, preferably MPLC and HPLC processes, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The substituted indole compounds according to the invention of the general formula I and corresponding stereoisomers as well as in each case the corresponding acids, bases, salts and solvates are toxicologically safe and are therefore suitable as pharmaceutical active ingredients in pharmaceutical preparations.

The present invention accordingly further provides pharmaceutical preparations which contain at least one substituted indole compound according to the invention of the general formula I, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or bases thereof or in the form of the salt thereof, in particular a physiologically acceptable salt, or in the form of the solvate thereof, in particular the hydrate, optionally together with physiologically acceptable auxiliary substances. It goes without saying that the pharmaceutical preparations according to the invention may also comprise mixtures of two or more of the above-stated compounds.

If the substituted indole compounds according to the invention of the general formula I or the corresponding physiologically acceptable bases, salts or solvates thereof are chiral, they may be present in the pharmaceutical preparation according to the invention, as already stated, preferably in the form of the racemates thereof, the pure enantiomers thereof, the pure diastereomers thereof, or in the form of a mixture of at least two of the above-stated stereoisomers.

The pharmaceutical preparations according to the invention are preferably suitable for combatting pain, preferably of chronic or neuropathic pain, and for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, preferably hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

The present invention also provides the use of at least one substituted indole compound of the general formula I, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, for the production of a pharmaceutical preparation for combatting pain, preferably of chronic or neuropathic pain, for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, particularly hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

The pharmaceutical preparations according to the invention may be present as liquid, semisolid or solid dosage forms, for example in the form of solutions for injection, drops, succi, syrups, sprays, suspensions, tablets, patches, capsules, transdermal delivery systems, suppositories, ointments, creams, lotions, gels, emulsions, aerosols or in multiparticulate form, for example in the form of pellets or granules, and also be administered as such.

In addition to at least one substituted indole compound according to the invention of the general formula I, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, suspending agents, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Compounds according to the invention of the general formula I, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, in a depot in dissolved form or in a dressing, optionally with the addition of skin penetration promoters, are suitable percutaneous administration preparations. Orally or percutaneously administrable formulations may also release the compounds according to the invention of the general formula I in delayed manner, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity to be administered to the patient of the respective substituted indole compound according to the invention of the general formula I, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, may vary and is for example dependent on the weight or age of the patient and on the mode of administration, the indication and the severity of the complaint. Conventionally, at least one substituted indole compound according to the invention of general formula I is administered in a quantity of 0.005 to 500 mg/kg, preferably of 0.05 to 5 mg/kg, of patient body weight, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate.

The investigation into the analgesic efficacy of the compounds according to the invention was performed by phenylquinone-induced writhing in mice, modified after I. C. Hendershot, J. Forsaith, J. Pharmacol. Exp. There. 125, 237240 (1959). The corresponding literature description is hereby introduced as a reference and is deemed to be part of the disclosure.

Male NMRI mice weighing from 25–30 g were used for this purpose. Groups of 10 animals per compound dose received, 10 minutes after intravenous administration of the compounds tested, 0.3 ml/mouse of a 0.02% aqueous solution of phenylquinone (phenylbenzoquinone, Sigma, Deisenhofen; solution prepared with addition of 5% of ethanol and stored in a water bath at 45° C.) administered intraperitoneally. The animals were then placed individually in observation cages. A push button counter was used to record the number of pain-induced stretching movements (writhing reactions=straightening of the torso with stretching of the rear extremities) for 5–20 minutes after phenylquinone administration. The control was provided by animals which received only physiological common salt solution with phenylquinone.

The compounds according to the invention were tested at the standard dosage of 10 mg/kg. The percentage inhibition (% inhibition) of the writhing reactions by a compound was calculated according to the following formula:

$$\% \text{ Inhibition} = 100 - \left[ \frac{\text{Writhing reaction, treated animals}}{\text{Writhing reaction, control}} \times 100 \right]$$

The invention is explained below with reference to Examples. These explanations are given merely by way of example and do not restrict the general concept of the invention.

EXAMPLES

The yields of the example compounds according to the invention were not optimised.

Example 1

Synthesis of 5-methyl-3-{[3'-(N,N-dimethylaminomethyl)-4'-hydroxy-4'-(3"-methoxyphenyl)-cyclohexylamino]-methyl}-1H-indole 2-carboxylic acid methyl ester 5-Methyl-3-formyl-1H-indole 2-carboxylic acid methyl ester (462 mg, 2 mmol) and 4-amino-2-(N,N-dimethylaminomethyl)-1-(3'-methoxyphenyl)-cyclohexan-1-ol (556 mg, 2 mmol) were dissolved in dry THF (5 ml) and 1,2-dichloroethane (15 ml), combined with calcined sodium sulfate (2 g) and stirred for 48 h at room temperature. Sodium triacetoxyborohydride (600 mg, 2.8 mmol) was then added and stirring was performed for a further 4 h. The sodium sulfate was removed by suction filtration, the solvent removed by vacuum distillation, the residue was dissolved in ethyl acetate (10 ml) and combined with 0.5 N HCl (10 ml). The phases were separated, the aqueous phase extracted with ethyl acetate (4×10 ml) and then adjusted to pH 8 with sodium hydrogencarbonate and extracted again with ethyl acetate (3×20 ml). After distillation of the solvent, the amine (810 mg, 82%) was obtained as a colourless solid. The melting point was 81–84° C.

Example 2

Synthesis of 4,6-dimethyl-3-{[3'-(N,N-dimethylaminomethyl)-4'-hydroxy-4'-(3"-methoxyphenyl)-cyclohexylamino]-methyl}-1H-indole 2-carboxylic acid ethyl ester Preparation proceeded in a manner similar to Example 1. 4,6-Dimethyl-3-formyl-1H-indole 2-carboxylic acid ethyl ester (981 mg, 4 mmol) and 4-amino-2-(N,N-dimethylaminomethyl)-1-(3'-methoxyphenyl)-cyclohexan-1-ol (1.112 g, 4 mmol) were dissolved in THF (16 ml) and 1,2-dichloroethane (60 ml). Dried sodium sulfate (4 g) was added thereto and stirred for 24 h, then sodium triacteoxyborohydride (2.4 g, 11.2 mmol) was added and stirring was performed for a further 2 h. For working up, the sodium sulfate was removed by suction filtration and washed with ethyl acetate (3×15 ml). The solution was combined with 1N HCl (15 ml) and stirred for 5 min. Subsequent to phase separation, the organic phase was extracted with 1N HCl (2×5 ml) and the aqueous phase was extracted with ethyl acetate (2×10 ml). The aqueous phase was adjusted to pH 8 with sodium hydrogencarbonate and extracted again with ethyl acetate (4×50 ml). After drying of the organic phase and removal of the solvent by distillation, 1.99 g (98%) of the coupling product were obtained. The melting point of the compound was 79–82° C.

Example 3

Synthesis of 5-chloro-3-{[3'-(N,N-dimethylaminomethyl)-4'-hydroxy-4'-(3"-methoxyphenyl)-cyclohexylamino]-methyl}-1H-indole 2-carboxylic acid ethyl ester.

Preparation proceeded in a manner similar to Example 1. Instead of 5-methyl-3-formyl-1H-indole 2-carboxylic acid methyl ester, 5-chloro-3-formyl-1H-indole 2-carboxylic acid methyl ester was reacted. The melting point of the compound was 84–87° C.

Example 4

Synthesis of 4,6-dichloro-3-{[3'-(N,N-dimethylaminomethyl)-4'-hydroxy-4'-(3"-methoxyphenyl)-cyclohexylamino]-methyl}-1H-indole 2-carboxylic acid ethyl ester Preparation proceeded in a manner similar to Example 1. 4,6-Dichloro-3-formyl-1H-indole 2-carboxylic acid ethyl ester and 4-amino-2-(N,N-dimethylaminomethyl)-1-(3'-methoxyphenyl)-cyclohexan-1-ol were stirred in THF with an excess of dried sodium sulfate for 72 h at 20° C. Without isolation of the imine, reduction with sodium triacteoxyborohydride was then performed within 24 h at 20° C. Yield was 90% after purification by column chromatography. The melting range of the compound was 71–81° C.

Example 5

Synthesis of 4,6-dimethyl-3-{[3'-N,N-dimethylaminomethyl)-4'-hydroxy-4'-(3"-methoxyphenyl)-cyclohexyl-(N-methylamino)]-methyl}-1H-indole 2-carboxylic acid ethyl ester 4,6-Dimethyl-3-formyl-1H-indole 2-carboxylic acid ethyl ester and 2-(N,N-dimethyl-aminomethyl)-1-(3'-methoxyphenyl)-4-N-methylamino)-cyclohexan-1-ol were reacted in a manner similar to Example 6. The melting point of the compound was 75–77° C.

Example 6

Synthesis of 4,6-dichloro-3-{[3'-N,N-dimethylaminomethyl)-4'-hydroxy-4'-(3"-methoxyphenyl)-cyclohexyl-(N-methylamino)]-methyl}-1H-indole 2-carboxylic acid ethyl ester 4,6-Dichloro-3-formyl-1H-indole 2-carboxylic acid ethyl ester (172 mg, 0.6 mmol) and 2-(N,N-dimethylaminomethyl)-1-(3'-methoxyphenyl)-4-(N-methylamino)-cyclohexan-1-ol (175 mg, 0.6 mmol) were dissolved in dry tetrahydrofuran (10 ml) and dry 1,2-dichloroethane (10 ml), combined with calcined sodium sulfate (2 g) and sodium triacetoxyborohydride (178 mg, 0.84 mmol) and stirred for 3 days. For working up, the solvent was removed by vacuum distillation, the residue was combined with ethyl acetate (10 ml), water (10 ml) and 10% sulfuric acid (2 ml), the phases were separated, the acidic aqueous phase was extracted with ethyl acetate (3×10 ml), adjusted to pH 7–8 with sodium hydrogencarbonate and again extracted with ethyl acetate (3×10 ml). After drying and removal of the solvent by distillation, the extract yielded 172 mg (51%) of a colourless solid with a melting point of 82–84° C.

Example 7

Synthesis of 5-chloro-3-{[3'-(N,N-dimethylaminomethyl)-4'-hydroxy-4'-(31"-methoxyphenyl)-cyclohexyl-(N-methylamino)]-methyl}-1H-indole 2-carboxylic acid ethyl ester 5-Chloro-3-formyl-1H-indole 2-carboxylic acid ethyl ester and 2-(N,N-dimethylaminomethyl)-1-(3'-methoxyphenyl)-4-(N-methylamino)-cyclohexan-1-ol were reacted in a manner similar to Example 6. The melting point of the compound was 72–74° C.

Example 8

Synthesis of 4,6-dichloro-3-[3'-hydroxy-3'-(3"-methoxyphenyl)-piperidin-1'-ylmethyl]-1H-indole 2-carboxylic acid ethyl ester 4,6-Dichloro-3-formyl-1H-indole 2-carboxylic acid ethyl ester (454 mg, 1.59 mmol) was dissolved in THF (15 ml) and 1,2-dichloroethane (15 ml). 3-(3'-Methoxyphenyl)-piperidin-3-ol (330 mg, 1.59 mmol) and sodium triacetoxyborohydride (477 mg, 2.22 mmol) were added and stirring was performed for 20 h at room temperature. The solvent was removed by distillation, the residue dissolved in ethyl acetate (10 ml) and combined with 10% sulfuric acid (2.5 ml) and water (10 ml). The phases were separated and the aqueous phase extracted with ethyl acetate (3×10 ml). The aqueous phase was adjusted to pH 7–8 with sodium hydrogencarbonate solution (15 ml) and extracted again with ethyl acetate (3×10 ml). After drying of the organic phase and removal of the solvent by distillation, 530 mg (70%) of a colourless solid were obtained. The melting point of the compound was 50–52° C.

Example 9

Synthesis of 4,6-dimethyl-3-[3'-hydroxy-3'-(3''-methoxyphenyl)-piperidin-1'-ylmethyl]-1H-indole 2-carboxylic acid ethyl ester 4,6-Dimethyl-3-formyl-1H-indole 2-carboxylic acid ethyl ester (355 mg, 1.45 mmol) was dissolved in THF (15 ml) and 1,2-dichloroethane (15 ml). 3-(3-Methoxyphenyl)-piperidin-3-ol (300 mg, 1.45 mmol) and sodium triacetoxyborohydride (429 mg, 2,03 mmol) were added and stirring was performed for 48 h at room temperature. The solvent was removed by distillation, the residue dissolved in ethyl acetate (10 ml) and combined with 10% sulfuric acid (2 ml) and water (10 ml), the phases were separated and the aqueous phase was extracted with ethyl acetate (3×10 ml). The aqueous phase was adjusted to pH 7–8 with sodium hydrogencarbonate solution (10 ml) and extracted again with ethyl acetate (4×10 ml). After drying of the organic phase and removal of the solvent by distillation, 370 mg (59%) of a colourless solid were obtained with a melting point at 70–72° C.

Example 10

Synthesis of 5-methyl-3-[3'-hydroxy-3'-(3''-methoxyphenyl)-piperidin-1'-ylmethyl]-1H-indole 2-carboxylic acid ethyl ester 5-Methyl-3-formyl-1H-indole 2-carboxylic acid ethyl ester (355 mg, 1.45 mmol) was dissolved in THF (15 ml) and 1,2-dichloroethane (15 ml), 3-(3'-methoxyphenyl)-piperidin-3-ol (300 mg, 1.45 mmol) and sodium triacetoxyborohydride (429 mg, 2.03 mmol) were added and stirring was performed for 48 h at room temperature. The solvent was removed by distillation, the residue dissolved in ethyl acetate (10 ml) and combined with 10% sulfuric acid (2 ml) and water (10 ml), the phases were separated and the aqueous phase was extracted with ethyl acetate (4×10 ml). The aqueous phase was adjusted to pH 7–8 with sodium hydrogencarbonate solution (10 ml) and extracted again with ethyl acetate (4×10 ml). After drying of the organic phase and removal of the solvent by distillation, 364 mg (60%) of a colourless solid were obtained with a melting point at 50–52° C.

Example 11

Synthesis of 5-chloro-3-[3'-hydroxy-3'-(3''-methoxyphenyl)-piperidin-1'-ylmethyl]-1H-indole 2-carboxylic acid ethyl ester 5-Chloro-3-formyl-1H-indole 2-carboxylic acid ethyl ester (439 mg, 1.74 mmol) was dissolved in THF (15 ml) and 1,2-dichloroethane (15 ml). 3-(3'-Methoxyphenyl)-piperidin-3-ol (361 mg, 1.74 mmol) and sodium triacetoxyborohydride (516 mg, 2.03 mmol) were added and stirring was performed for 48 h at room temperature. The solvent was removed by distillation, the residue dissolved in ethyl acetate (10 ml) and combined with 10% sulfuric acid (3 ml) and water (10 ml), the phases were separated and the aqueous phase was extracted with ethyl acetate (4×10 ml). The aqueous phase was adjusted to pH 7–8 with sodium hydrogencarbonate solution (15 ml) and extracted again with ethyl acetate (4×10 ml). After drying of the organic phase and removal of the solvent by distillation, 465 mg (60%) of a colourless solid were obtained with a melting point at 60–62° C.

Example 12

Synthesis of 5-methyl-3-{[3'-(N,N-dimethylaminomethyl)-4'-hydroxy-4'-(31''-methoxyphenyl)-cyclohexylamino]-methyl)-1H-indole 2-carboxylic acid 5-Methyl-3-([3'-(N,N-dimethylaminomethyl)-4'-hydroxy-4'-(3''-methoxyphenyl)-cyclohexylamino]-methyl}-1H-indole 2-carboxylic acid methyl ester from Example 1 (800 mg, 1.62 mmol) was dissolved in ethanol (10 ml), combined with 1N KOH (3.24 ml, 3.24 mmol) and water (4 ml) and stirred for 10 h at 60° C. Ethanol was removed by vacuum distillation and the residue combined with water (10 ml). By careful addition of 1N HCl (2 ml), the pH value of the mixture was adjusted to 7–8. The consistency of the solid varied markedly from unctuous to crystalline. The solid was removed by suction filtration, washed with water and vacuum-dried over phosphorus pentoxide. A colourless substance (515 mg, 68%) with a melting point of 167–168° was obtained.

Example 13

Synthesis of 5-chloro-3-{[3'-(N,N-dimethylaminomethyl)-4'-hydroxy-4'-(3''-methoxyphenyl)-cyclohexylamino]-methyl}-1H-indole 2-carboxylic acid Preparation proceeded from 5-chloro-3-{[3'-(N,N-dimethylaminomethyl)-4'-hydroxy-4'-(3''-methoxyphenyl)-cyclohexylamino]-methyl}-1H-indole 2-carboxylic acid ethyl ester in a manner similar to Example 12. The melting point of the compound was 232–234° C.

Example 14

Synthesis of 4,6-dimethyl-3-{[3'-(N,N-dimethylaminomethyl)-4'-hydroxy-4'-(3''-methoxyphenyl)-cyclohexylamino]-methyl}-1H-indole 2-carboxylic acid Preparation proceeded from 4,6-dimethyl-3-{[3'-(N,N-dimethylaminomethyl)-4'-hydroxy-4'-(3''-methoxyphenyl)-cyclohexylamino]-methyl}-1H-indole 2-carboxylic acid ethyl ester in a manner similar to Example 12. The melting point of the compound was 259–262° C.

Example 15

Synthesis of 4,6-dichloro-3-{[3'-(N,N-dimethylaminomethyl)-4'-hydroxy-4'-(3''-methoxyphenyl)-cyclohexylamino]-methyl}-1H-indole 2-carboxylic acid Preparation proceeded from 4,6-dichloro-3-[3'-(N,N-dimethylaminomethyl)-4'-hydroxy-4'-(3''-methoxyphenyl)-cyclohexylamino]-methyl}-1H-indole 2-carboxylic acid ethyl ester in a manner similar to Example 12.

Example 16

Synthesis of 4,6-dichloro-3-[3'-hydroxy-3'-(3''-methoxyphenyl)-piperidin-1'-ylmethyl]-1H-indole 2-carboxylic acid Preparation proceeded from 4,6-dichloro-3-[3'-hydroxy-3'-(3''-methoxyphenyl)-piperidin-1'-ylmethyl]-1H-indole 2-carboxylic acid ethyl ester in a manner similar to Example 12. The compound had two melting ranges of 190–205° C. and 240–243° C.

Example 17

Synthesis of 5-chloro-3-[3'-hydroxy-3'-(3''-methoxyphenyl)-piperidin-1'-ylmethyl]-1H-indole 2-carboxylic acid Preparation proceeded from 5-chloro-3-[3'-hydroxy-3'-(3''-methoxyphenyl)-piperidin-1'-ylmethyl]-1H-indole 2-carboxylic acid ethyl ester in a manner similar to Example 12. The compound had a melting range of 189–192° C.

Example 18

Synthesis of 4,6-dichloro-3-{[4'-hydroxy-4'-(3''-methoxyphenyl)-cyclohexylamino]-methyl}-1H-indole 2-carboxylic acid ethyl ester Preparation proceeded in a manner similar to Example 1. 4,6-Dichloro-3-formyl-1H-indole 2-carboxylic acid ethyl ester was reacted with 4-amino-1-(3'-methoxyphenyl)-cyclohexan-1-ol. The melting point of the compound was 138–140° C.

Example 19

Synthesis of 4,6-dichloro-3-({[4'-hydroxy-4'-(3''-methoxyphenyl)-cyclohexyl]-(N-methylamino)}-methyl)-1H-indole 2-carboxylic acid ethyl ester Preparation proceeded in a manner similar to Example 1. 4,6-Dichloro-3-formyl-1H-indole 2-carboxylic acid ethyl ester was reacted with 1-(3'-methoxyphenyl)-4-(N-methylamino)-cyclohexan-1-ol. The melting point of the compound was 55–57° C.

Example 20

Synthesis of 4,6-dichloro-3-({[2'-hydroxy-2'-(3''-methoxyphenyl)-cyclohexylmethyl]-amino}-methyl-1H-indole 2-carboxylic acid ethyl ester 4,6-Dichloro-3-formyl-1H-indole 2-carboxylic acid ethyl ester (514 mg, 1.79 mmol) was dissolved in THF (20 ml) and 1,2-dichloroethane (20 ml), combined with 2-(aminomethyl)-1-(3'-methoxyphenyl)-cyclohexan-1-ol (423 mg, 1.79 mmol) and calcined sodium sulfate (4 g) and stirred for 3 days at room temperature. Sodium triacetoxyborohydride (758 mg, 3.58 mmol) was added and stirring was performed for a further 2 h. For working up, sodium hydrogencarbonate solution (20 ml) was added, the phases were separated, the aqueous phase was extracted with diethyl ether (3×20 ml) and the combined organic phases were extracted with sodium hydrogencarbonate solution (2×5 ml), the organic phase was dried over sodium sulfate, the solvent removed by distillation and 971 mg of crude product were obtained. The crude product was recrystallised from ethyl acetate/ethanol (20: 1.15 ml). Yield was 749 mg (83%). The compound was obtained as a colourless solid with a melting point of 185–188° C.

Example 21

Synthesis of 5-chloro-3-({[2'-hydroxy-2'-(3''-methoxyphenyl)-cyclohexylmethyl]-amino}-methyl)-1H-indole 2-carboxylic acid ethyl ester 5-Chloro-3-formyl-1H-indole 2-carboxylic acid ethyl ester (851 mg, 3.37 mmol) was dissolved in THF (20 ml) and 1,2-dichloroethane (20 ml), combined with 2-(aminomethyl)-1-(3'-methoxyphenyl)-cyclohexan-1-ol (795 mg, 3.37 mmol) and calcined sodium sulfate (3 g) and stirred for 48 h at room temperature. Sodium triacetoxyborohydride (1 g, 4.7 mmol) was then added, stirring performed for a further 6 h, the sodium sulfate removed by suction filtration, the solvent removed by distillation and the residue dissolved in ethyl acetate (10 ml). After addition of 1N sulfuric acid (3 ml) and water (10 ml), the phases were separated and the aqueous phase extracted with ethyl acetate (8×10 ml). The aqueous phase was adjusted to pH 8 with sodium hydrogencarbonate and extracted again with ethyl acetate (4×10 ml). The solvent was removed. Yield was 740 mg (47%). The melting point of the compound was 157–158° C.

Example 22

Synthesis of 4,6-dimethyl-3-({[2'-hydroxy-2'-(3''-methoxyphenyl)-cyclohexylmethyl]-amino}-methyl)-1H-indole 2-carboxylic acid ethyl ester 4,6-Dimethyl-3-formyl-1H-indole 2-carboxylic acid ethyl ester (491 mg, 2 mmol) was dissolved in THF (20 ml) and 1,2-dichloroethane (20 ml), combined with 2-(aminomethyl)-1-(3'-methoxyphenyl)-cyclohexan-1-ol (471 mg, 2 mmol) and dried sodium sulfate (4 g) and stirred for 48 h at room temperature. After addition of sodium triacetoxyborohydride (600 mg, 2.8 mmol), stirring was performed for a further 3 h. The sodium sulfate was removed by suction filtration and the solvent removed by distillation. The residue was chromatographed on silica gel (90 g silica gel, 900 ml ethyl acetate/ethanol 20:1) and yielded 468 mg (50%) of a colourless solid with a melting point of 114–116° C.

Example 23

Synthesis of 5-methyl-3-({[2'-hydroxy-2'-(3''-methoxyphenyl)-cyclohexylmethyl]-amino}-methyl)-1H-indole 2-carboxylic acid ethyl ester 5-Methyl-3-formyl-1H-indole 2-carboxylic acid ethyl ester (462 mg, 2 mmol) was dissolved in THF (20 ml) and 1,2-dichloroethane (20 ml), combined with 2-(aminomethyl)-1-(3'-methoxyphenyl)-cyclohexan-1-ol (471 mg, 2 mmol) and calcined sodium sulfate (4 g) and stirred for 48 h at room temperature. After addition of sodium triacetoxyborohydride (600 mg, 2.8 mmol), stirring was performed for a further 3 h. The sodium sulfate was removed by suction filtration and the solvent removed by distillation. The residue was combined with sodium hydrogencarbonate and diethyl ether, the aqueous phase extracted with diethyl ether (4×20 ml), the extract dried and evaporated. The residue was treated with ethyl acetate/ethanol (10 ml, 20:1). Part of the substance dissolved. The undissolved part was clean ester (283 mg, 31%). From the dissolved part, a further 218 mg (24%) were obtained by chromatography on silica gel, (90 g silica gel, 900 ml ethyl acetate/ethanol, 20:1). Total yield amounted to 501 mg (55%). The colourless solid had a melting point of 201–204° C.

Example 24

Synthesis of 4,6-dichloro-3-({[2'-hydroxy-2'-(31'-hydroxyphenyl)-cyclohexylmethyl]-amino}-methyl)-1H-indole 2-carboxylic acid ethyl ester hydrochloride 4,6-Dichloro-3-formyl-1H-indole 2-carboxylic acid ethyl ester (280 mg, 0.98 mmol) was dissolved in THF (20 ml), combined with 2-(aminomethyl)-1-(3'-hydroxyphenyl)-cyclohexan-1-ol (217 mg, 0.98 mmol) and dried sodium sulfate (2 g) and stirred for 48 h at room temperature. Sodium triacetoxyborohydride (300 mg, 1.4 mmol) was then added and stirring was performed again for 3 h. The sodium sulfate was removed by suction filtration, washed with ethyl acetate (3×10 ml), the filtrate combined with 1N HCl (5 ml), the organic phase extracted with 1N HCl (2×2 ml) and the aqueous phase extracted with ethyl acetate (2×10 ml). The aqueous phase was adjusted to pH 7 with sodium hydrogencarbonate solution (30 ml) and extracted again with ethyl acetate (5×10 ml). The organic phase was dried and the solvent removed by distillation. 299 mg (62%) of an oil were obtained. It was possible to convert the oil into a crystalline hydrochloride with a melting point of 175–178° C. by stirring (5 h) with trimethylchlorosilane (0.112 ml, 0.885 mmol) in methyl ethyl ketone (5 ml).

Example 25

Synthesis of 5-chloro-3-({[2'-hydroxy-2'-(3''-hydroxyphenyl)-cyclohexylmethyl]-amino}-methyl)-1H-indole 2-carboxylic acid ethyl ester 5-Chloro-3-formyl-1H-indole 2-carboxylic acid ethyl ester (504 mg, 2 mmol) was dissolved in THF (20 ml), combined with 2-(aminomethyl)-1-(3'-hydroxyphenyl)-cyclohexan-1-ol (443 mg, 2 mmol) and dried sodium sulfate (2 g) and stirred for 48 h at room temperature. Sodium triacetoxyborohydride (600 mg, 2.8 mmol) was then added and stirring was performed again for 6 h. The sodium sulfate was removed by suction filtration, the solvent removed by distillation, the residue dissolved in ethyl acetate (10 ml), combined with 10% sulfuric acid (2 ml) and water (10 ml), the phases were separated and the aqueous phase was extracted with ethyl acetate (5×10 ml). The aqueous phase was adjusted to pH 7 with sodium hydrogencarbonate solution (10 ml) and extracted again with ethyl acetate (5×10 ml). The organic phase was dried and the solvent removed by distillation. The crude product obtained was chromatographed (20 g silica gel, 200 ml ethyl acetate/ethanol, 20:1) and yielded 244 mg (26%) of a colourless solid with a melting point of 88–90° C.

Example 26

Synthesis of 4,6-dimethyl-3-({[2'-hydroxy-2'-(3''-hydroxyphenyl)-cyclohexylmethyl]-amino}-methyl)-1H-indole 2-carboxylic acid ethyl ester 4,6-Dichloro-3-formyl-1H-indole 2-carboxylic acid ethyl ester (485 mg, 1.98 mmol) was dissolved in THF (40 ml). 2-(Aminomethyl)-1-(3'-hydroxyphenyl)-cyclohexan-1-ol (438 mg, 1.98 mmol) and sodium sulfate (4 g) were added and stirring was performed for 72 h at room temperature. The sodium sulfate was removed by suction filtration, the solvent removed by distillation, the residue dissolved in ethyl acetate (20 ml), combined with 10% sulfuric acid (3 ml) and water (10 ml). A solid precipitated out, which was removed by suction filtration. The aqueous phase was extracted with ethyl acetate (3×10 ml), the aqueous phase adjusted to pH 7–8 with sodium hydrogencarbonate solution and extraction performed again with ethyl acetate (4×10 ml). The solvent was removed from the organic phase. Yield was 720 mg (81%). The melting point of the compound was 168–170° C.

Example 27

Synthesis of 5-methyl-3-({[2'-hydroxy-2'-(3''-hydroxyphenyl)-cyclohexylmethyl]-amino}-methyl)-1H-indole 2-carboxylic acid ethyl ester 5-Methyl-3-formyl-1H-indole 2-carboxylic acid ethyl ester (376 mg, 1.63 mmol) was dissolved in THF (20 ml), combined with 2-(aminomethyl)-1-(3'-hydroxyphenyl)-cyclohexan-1-ol (360 mg, 1.63 mmol) and dried sodium sulfate (3 g) and stirred for 48 h. Sodium triacetoxyborohydride (482 mg, 2.28 mmol) was added and stirring was performed for a further 4 h. For working up, the sodium sulfate was removed by suction filtration, the solvent removed by distillation, the residue combined with sodium hydrogencarbonate solution (20 ml) and ethyl acetate (20 ml), the phases were separated, the aqueous phase was extracted with ethyl acetate (3×20 ml), the organic phase dried over sodium sulfate and the solvent removed by distillation. The residue was chromatographed (60 g silica gel, 600 ml ethyl acetate/ethanol, 20:1). It was possible to obtain 360 mg (51%) of a colourless solid with a melting point of 178–180° C.

Example 28

Synthesis of 4,6-dichloro-3-({[2'-hydroxy-2'-(3''-methoxyphenyl)-cyclohexylmethyl]-amino}-methyl)-1H-indole 2-carboxylic acid 4,6-Dichloro-3-({[2'-hydroxy-2'-(3''-methoxyphenyl)-cyclohexylmethyl]-amino}-methyl)-1H-indole 2-carboxylic acid ethyl ester from Example 23 (177 mg, 0.35 mmol) was dissolved in THF (5 ml) and ethanol-(10 ml), combined with 1N KOH (0.7 ml, 0.7 mmol) and water (2 ml) and stirred for 3.5 h at 60° C. For working up, the solvent was removed by distillation, and the semisolid residue was combined with water (10 ml) and adjusted to pH 7 with 1N HCl (0.55 ml, 0.55 mmol). The solid formed was removed by suction filtration, washed with water and dried over $P_2O_5$. Yield was 147 mg (88%). The melting point of the compound was 244–245° C.

Example 29

Synthesis of 5-chloro-3-({[2'-hydroxy-2'-(3''-methoxyphenyl)-cyclohexylmethyl]-amino}-methyl)-1H-indole 2-carboxylic acid 5-Chloro-3-({[2'-hydroxy-2'-(3''-methoxyphenyl)-cyclohexylmethyl]-amino}-methyl)-1H-indole 2-carboxylic acid ethyl ester (360 mg, 0.764 mmol) was suspended in ethanol (12 ml), combined with 1N KOH (1.53 ml, 1.53 mmol) and stirred at 60° C. for 6 h. After removal of the solvent by distillation, the residue was combined with water (10 ml) and neutralised with 1N HCl. The solid formed was removed by suction filtration and dried. Yield was 290 mg (86%). The melting point of the compound was 242–243° C.

Example 30

Synthesis of 4,6-dimethyl-3-({[2'-hydroxy-2'-(3''-methoxyphenyl)-cyclohexylmethyl]-amino}-methyl)-1H-indole 2-carboxylic acid 4,6-Dimethyl-3-({[2'-hydroxy-2$^1$-(3''-methoxyphenyl)-cyclohexylmethyl]-amino}-methyl)-1H-indole 2-carboxylic acid ethyl ester (200 mg. 0.43 mmol) was dissolved in ethanol (5 ml), combined with 1N KOH (0.86 ml, 0.86 mmol) and water (0.4 ml) and stirred for 5 h at 60° C. After removal of the solvent by distillation, addition of water (10 ml) and neutralisation with 1N HCl, the solid formed was removed by suction filtration, washed and dried. Yield was 127 mg (68%). The compound was obtained as a colourless solid with a melting point of 210–213° C.

Example 31

Synthesis of 5-methyl-3-({[2'-hydroxy-2'-(3"-methoxyphenyl)-cyclohexylmethyl]-amino}-methyl)-1H-indole 2-carboxylic acid 5-Methyl-3-({[2'-hydroxy-2'-(3"-methoxyphenyl)-cyclohexylmethyl]-amino}-methyl)-1H-indole 2-carboxylic acid ethyl ester (250 mg, 0.55 mmol) was suspended in ethanol (10 ml), combined with 1N KOH (1.1 ml, 1.10 mmol) and water (2 ml) and stirred for 6 h at 60° C. After removal of the solvent by distillation, addition of water (10 ml) and neutralisation with 1N HCl, the precipitated solid was removed by suction filtration, washed and dried. Yield was 209 mg (89%). The melting point of the compound was 217–219° C.

Example 32

Synthesis of 4,6-dichloro-3-({[2'-hydroxy-2'-(3"-hydroxyphenyl)-cyclohexylmethyl]-amino}-methyl)-1H-indole 2-carboxylic acid 4,6-Dichloro-3-({[2'-hydroxy-2'-(3"-hydroxyphenyl)-cyclohexylmethyl]-amino}-methyl)-1H-indole 2-carboxylic acid ethyl ester was suspended in ethanol, combined with 1N KOH and water and stirred for 6 h at 60° C. After removal of the solvent by distillation, addition of water (10 ml) and neutralisation with 1N HCl, the precipitated solid was removed by suction filtration, washed and dried. Yield was 201 mg (88%). The melting point of the compound was 230–232° C.

Example 33

Synthesis of 5-chloro-3-({[2'-hydroxy-2'-(3"-hydroxyphenyl)-cyclohexylmethyl]-amino}-methyl)-1H-indole 2-carboxylic acid 5-Chloro-3-({[2'-hydroxy-2'-(3"-hydroxyphenyl)-cyclohexylmethyl]-amino}-methyl)-1H-indole 2-carboxylic acid ethyl ester (90 mg, 0.197 mmol) was dissolved in ethanol (5 ml), combined with 1N KOH (0.4 ml, 0.4 mmol) and water (2 ml) and stirred for 6 h at 60° C. Ethanol was removed by distillation, the residue combined with water (10 ml) and adjusted to pH 7 with 1N HCl. The solid formed was removed by suction filtration and dried. Yield was 63 mg (75%). The melting point of the compound was 201–203° C.

Example 34

Synthesis of 4,6-dichloro-3-[(1',5'-dimethyl-3'-oxo-2'-phenyl-2',3'-dihydro-1'H-pyrazol-4'-ylamino)-methyl]-1H-indole 2-carboxylic acid ethyl ester 4,6-Dichloro-3-formyl-1H-indole 2-carboxylic acid ethyl ester (286 mg, 1.0 mol) and 4-aminoantipyrine (203 mg, 1.0 mmol) were dissolved in dry tetrahydrofuran (10 ml), combined with calcined sodium sulfate (2 g) and stirred for 3 days. Sodium triacetoxyborohydride (300 mg, 1.4 mmol) and dry 1,2-dichloroethane (10 ml) were then added and stirring was performed for a further 3 h. For working up, the solvent was removed by vacuum distillation and the residue was combined with ethyl acetate (10 ml), water (10 ml) and sodium hydrogencarbonate solution (10 ml). A solid precipitated out, which was removed by suction filtration. After drying, 370 mg (79%) of a colourless solid with a melting point of 202–204° were obtained.

Example 35

Synthesis of 4,6-dimethyl-3-[(1',5'-dimethyl-3'-oxo-2'-phenyl-2',3'-dihydro-1'H-pyrazol-4'-ylamino)-methyl]-1H-indole 2-carboxylic acid ethyl ester 4,6-Dimethyl-3-formyl-1H-indole 2-carboxylic acid ethyl ester (736 mg, 3.0 mol) and 4-aminoantipyrine (610 mg, 3.0 mmol) were dissolved in dry tetrahydrofuran (10 ml), combined with calcined sodium sulfate (3 g) and stirred for 3 days. Sodium triacetoxyborohydride (900 mg, 4.2 mmol) and dry 1,2-dichloroethane (10 ml) were then added and stirring was performed for a further 3 h. For working up, the solvent was removed by vacuum distillation and the residue was combined with ethyl acetate (10 ml), water (10 ml) and sodium hydrogencarbonate solution (10 ml). A solid precipitated out, which was removed by suction filtration. Yield was 384 mg (79%). The colourless solid had a melting point of 200–202° C.

Example 36

Synthesis of 4,6-dichloro-3-[4'-(4"-chlorophenyl)-4'-hydroxypiperidin-1'-ylmethyl]-1H-indole 2-carboxylic acid ethyl ester 4,6-Dichloro-3-formyl-1H-indole 2-carboxylic acid ethyl ester (858 mg, 3 mmol) and 4-(4'-chlorophenyl)-piperidin-4-ol (635 mg, 3 mmol) were dissolved in dry tetrahydrofuran (20 ml), combined with calcined sodium sulfate (2 g) and stirred for 48 h at room temperature. Dry 1,2-dichloroethane (10 ml) and sodium triacetoxyborohydride (900 mg) were then added and stirring was performed for a further 3 h. For working up, the solvent was removed by vacuum distillation and the residue was combined with water (10 ml), 1N sulfuric acid (2 ml) and ethyl acetate (10 ml). The precipitated solid was removed by suction filtration, washed with water and dried. 1.13 g of the product were obtained. The melting point of the compound was 64–66° C.

Example 37

Synthesis of 4,6-dimethyl-3-[4'-(4"-chlorophenyl)-4'-hydroxypiperidin-1'-ylmethyl]-1H-indole 2-carboxylic acid ethyl ester 4,6-Dimethyl-3-formyl-1H-indole 2-carboxylic acid ethyl ester (1.47 mg, 6 mmol) and 4-(4'-chlorophenyl)-piperidin-4-ol (1.27 mg, 6 mmol) were dissolved in dry tetrahydrofuran (30 ml), combined with calcined sodium sulfate (4 g) and stirred for 24 h at room temperature. Dry 1,2-dichloroethane (20 ml) and sodium triacetoxyborohydride (1.78 g, 8.4 mmol) were then added and stirring was performed for a further 3 h at room temperature. After removal of the solvent by vacuum distillation, the residue was-combined with sodium hydrogencarbonate solution (30 ml) and ethyl acetate (20 ml) and stirred for 15 min., the phases were separated and the aqueous phase was extracted with ethyl acetate (3×20 ml). The organic phase was dried and the solvent was removed therefrom. Yield was 1.54 mg (58%). The melting point of the compound was 65–67° C.

Example 38

Synthesis of 4,6-dichloro-3-(6',7'-dimethoxy-3',4'-dihydro-1'H-isoquinolin-2'-ylmethyl)-1H-indole 2-carboxylic acid ethyl ester hydrochloride 6,7-Dimethoxy-3,4-dihydro-1H-isoquinoline (204 mg, 1.05 mmol) and 4,6-dichloro-3-formyl-1H-indole 2-carboxylic acid ethyl ester (300 mg, 1.05 mmol) were dissolved in THF (10 ml) and after 10 minutes the solution was combined with sodium triacetoxyborohydride (300 mg, 1.4 mmol) and stirred for 22 h. The solvent was removed, and the residue combined with diethyl ether (20 ml) and 0.5N HCl (20 ml, 10 mmol) and stirred for 1 h. The hydrochloride crystallised out and, after washing with diethyl ether and water, could be obtained as a white solid with a melting point of 173–176° in a yield of 83%.

Example 39

Synthesis of 4,6-methyl-3-(6',7'-dimethoxy-3',4'-dihydro-1'H-isoquinolin-2'-ylmethyl)-1H-indole 2-carboxylic acid ethyl ester hydrochloride 4,6-Dimethyl-3-formyl-1H-indole 2-carboxylic acid ethyl ester (637 mg, 2.6 mmol) and 6,7-dimethoxy-3,4-dihydro-1H-isoquinoline (510 mg, 2.6 mmol) were dissolved in tetrahydrofuran (25 ml), combined after 10 minutes with NaBH(OAc)$_3$ (780 mg, 364 mmol) and stirred for 72 h. The reaction mixture was evaporated and the residue combined with diethyl ether (40 ml) and 1N hydrochloric acid (26 ml, 26 mmol) and stirred for 1 h. The precipitated hydrochloride was washed with diethyl ether and water. The product could be obtained as a beige-coloured solid with a melting point of 199–203° C. in pure form in a yield of 76%.

Example 40

Synthesis of 4,6-dichloro-3-[4'-(3"-methoxyphenyl)-piperazin-1'-ylmethyl]-1H-indole 2-carboxylic acid ethyl ester dihydrochloride 1-(3'-Methoxyphenyl)-piperazine (360 mg, 1.88 mmol) and 4,6-dichloro-3-formyl-1H-indole 2-carboxylic acid ethyl ester (537 mg, 1.88 mmol) were dissolved in THF (18 ml) and combined with NaBH(OAc)$_3$ (540 mg, 2.52 mmol) after 10 min. After 22 h no conversion appeared to have taken place, such that NaBH(OAc)$_3$ (540 mg, 2.52 mmol) was again added, together with anhydrous sodium sulfate (3.8 g). After a further reaction time of 67 h, the reaction mixture was evaporated, the residue resuspended in diethyl ether (40 ml) and 0.5N HCl (50 ml, 25 mmol) and stirred for 1 h. The precipitated dihydrochloride was filtered out and washed with diethyl ether and water. The product could be obtained as a beige-coloured solid with a melting point of 169–172° C. in a yield of 85%.

Example 41

Synthesis of 4,6-Dichloro-3-(4'-carbamoyl-[1",4'] bipiperidin-1'-ylmethyl)-1H-indole 2-carboxylic acid ethyl ester

[1,4']-Bipiperidinyl-carboxylic acid amide (423 mg, 2 mmol) and 4,6-dichloro-3-formyl-1H-indole 2-carboxylic acid ethyl ester (572 mg, 2 mmol) were dissolved in THF (20 ml); after 10 minutes NaBH(OAc)$_3$ (600 mg, 2.8 mmol) was added and stirring was performed for 24 h. The mixture was evaporated, the residue resuspended in diethyl ether (40 ml) and in 0.5N hydrochloric acid (40 ml, 20 mmol) and stirred for 2 h, wherein the dihydrochloride precipitated out as the crude product. The solid was removed by suction filtration and washed with diethyl ether. Further purification with water was not possible because of the good solubility of the dihydrochloride. The dihydrochloride was resuspended in ethanol (60 ml), a clear solution not being obtained, was combined with 5% NaHCO$_3$ solution (30 ml) combined and stirring was performed for 1 h. A white solid was removed by suction filtration and washed with ethanol and water. The product was obtained in a yield of 44% and had a melting point of 212–215° C.

Example 42

Synthesis of 4,6-dichloro-3-{[(4'-benzyl-4'-(N,N-dimethylamino)-cyclohexyl)-(N-propylamino)]-methyl}-1H-indole 2-carboxylic acid ethyl ester dihydrochloride 4,6-Dichloro-3-formyl-1H-indole 2-carboxylic acid ethyl ester (519 mg, 1.81 mmol) and 1-benzyl-1-(N,N-dimethylamino)-4-(N-propylamino)-cyclohexane (500 mg, 1.81 mmol) were dissolved under argon in THF (18 ml) and combined with Na$_2$SO$_4$ (3.62 g). After 15 minutes, NaBH(OAc) 3 was added as reducing agent and the mixture stirred for 23 h. The solvent was removed, the residue resuspended in diethyl ether (40 ml) and 1N HCl (18 ml, 18 mmol) and stirred for 2 h. Only after 3 days could the hydrochloride be isolated as a solid. The solid was filtered out and washed with diethyl ether. For further purification, the hydrochloride was resuspended in ethyl acetate (60 ml), combined with 5% NaHCO$_3$ solution (20 ml) and stirred. After evaporation, the free base was obtained in a yield of 49%.

The dihydrochloride could be obtained as a white solid with a melting point of 165–169° C. in a yield of 39% after 1 h reaction time by resuspending the base in ethyl methyl ketone (15 ml) and adding ClSiMe$_3$ (0.132 ml, 1.05 mmol).

Example 43

Synthesis of 4,6-dichloro-3-[(1',5'-dimethyl-3'-oxo-2'-phenyl-2',3'-dihydro-1'H-pyrazol-4'-ylamino)-methyl]-1H-indole 2-carboxylic acid 4,6-Dichloro-3-[(1',5'-dimethyl-3'-oxo-2'-phenyl-2',3'-dihydro-1'H-pyrazol-4'-ylamino)-methyl]-1H-indole 2-carboxylic acid ethyl ester (370 mg, 0.781 mmol) was dissolved in ethanol (10 ml), combined with 1N KOH (2.6 ml, 2.6 mmol) and water (2 ml) and stirred for 3 h at 60° C. The solvent was removed, the residue combined with water (10 ml) and adjusted to pH 6 with 1N HCl. The solid formed was removed by suction filtration and washed with water. After vacuum-drying, 233 mg (67%) of the product were obtained. The product had a melting point of 265–268° C.

Example 44

Synthesis of 4,6-dichloro-3-[4'-(4"-chlorophenyl)-4'-hydroxypiperidin-1'-ylmethyl]-1H-indole 2-carboxylic acid 4,6-Dichloro-3-[4'-(4"-chlorophenyl)-4'-hydroxypiperidin-1'-ylmethyl]-1H-indole 2-carboxylic acid ethyl ester (300 mg, 0.62 mmol) was dissolved in ethanol (10 ml) and combined with 1N KOH (1.25 ml, 1.25 mmol) and water (2 ml). The mixture was stirred for 4 h at 60°, wherein it acquired a pink colour. The solvent was removed by distillation, the residue combined with water (10 ml) and adjusted to pH 6 with 1N HCl. It was possible to obtain by suction filtration 193 mg (68%) of a pale pink solid with a melting point of 170–174° C.

Example 45

Synthesis of 4,6-dimethyl-3-[4'-(4"-chlorophenyl)-4'-hydroxypiperidin-1'-ylmethyl]-1H-indole 2-carboxylic acid 4,6-Dimethyl-3-[4'-(4"-chlorophenyl)-4'-hydroxypiperidin-1'-ylmethyl]-1H-indole 2-carboxylic acid ethyl ester (300 mg, 0.68 mmol) was dissolved in ethanol (10 ml), combined with 1N KOH (2.36 mol, 2.36 mmol) and water (1 ml) and stirred for 4 h at 60° C. The mixture developed a red colour. For working up, the solvent was removed by vacuum distillation, the residue combined with water (10 ml) and adjusted to pH 6 with 1N HCl. It was possible to obtain 190 mg (68%) of a yellow solid with a melting point of 194–197° C.

Example 46

Synthesis of 4,6-dichloro-3-[4'-(3"-methoxyphenyl)-piperazin-1'-ylmethyl]-1H-indole 2-carboxylic acid dihydrochloride 4,6-Dichloro-3-[4'-(3"-methoxyphenyl)-piperazin-1'-ylmethyl]-1H-indole 2-carboxylic acid ethyl ester dihydrochloride (485 mg, 0.9 mmol) was dissolved in ethanol (60 ml) and combined with 1.7N KOH (16 ml, 27 mmol) for hydrolysis. After 16 hours' reaction time, the mixture was evaporated, the potassium salt of 4,6-dichloro-3-[4'-(3"-methoxyphenyl)-piperazin-1'-ylmethyl]-1H-indole 2-carboxylic acid extracted with ethyl acetate and the dihydrochloride of 4,6-dichloro-3-[4'-3"-methoxyphenyl)-piperazin-1'-ylmethyl]-1H-indole 2-carboxylic acid was formed as a precipitate by the addition of 1.8N ethanolic HCl (3 ml, 5.4 mmol). The solid was removed by suction filtration, the filtrate was further evaporated and the residue washed with water (10 ml). The product was obtained as a grey solid with a melting point of 177–182° in a yield of 86%.

Example 47

Synthesis of 4,6-dichloro-3-(6',7'-dimethoxy-3',4'-dihydro-1'H-isoquinolin-2'-ylmethyl)-1H-indole 2-carboxylic acid hydrochloride 4,6-Dichloro-3-(6',7'-dimethoxy-3',4'-dihydro-1'H-isoquinolin-2'-ylmethyl)-1H-indole 2-carboxylic acid ethyl ester (460 mg, 0,92 mmol) was dissolved in ethanol (20 ml), combined with 1.7N KOH (11.4 ml, 20 mmol) and reacted for 20 h. After evaporation of the reaction mixture, the residue was combined with ethyl acetate, wherein the potassium salt of 4,6-dichloro-3-(6',7'-dimethoxy-3',4'-dihydro-1'-isoquinoline-2'-ylmethyl)-1H-indole 2-carboxylic acid precipitated after a few minutes. The potassium salt was filtered out, the filtrate evaporated and filtered again. The solid was dissolved in ethyl methyl ketone (15 ml) and combined with 1.8N ethanolic HCl (1.15 ml, 2.08 mmol). After cooling to −10° C., the solution was evaporated. The hydrochloride of 4,6-dichloro-3-(6',7'-dimethoxy-3',4'-dihydro-1'H-isoquinolin-2'-ylmethyl)-1H-indole 2-carboxylic acid precipitated out together with KCl and was filtered out. The solid was washed with water (5 ml). The product was obtained with a yield of 80%. The beige-coloured solid had a melting point of 186–192° C.

Example 48

Synthesis of 4,6-dimethyl-3-(6',7'-dimethoxy-3',4'-dihydro-1'H-isoquinolin-2'-ylmethyl)-1H-indole 2-carboxylic acid hydrochloride 4,6-Dimethyl-3-(6',7'-dimethoxy-3',4'-dihydro-1'H-isoquinolin-2'-ylmethyl)-1H-indole 2-carboxylic acid ethyl ester (300 mg, 0,71 mmol) was dissolved in ethanol (60 ml), combined with 1.7N KOH (4.17 ml, 7.1 mmol) and reacted for 88 h. After evaporation of the mixture, the potassium salt obtained of 4,6-dimethyl-3-(6',7'-dimethoxy-3',4'-dihydro-1'-isoquinolin-2'-ylmethyl)-1H-indole 2-carboxylic acid was combined with ethyl acetate and 1.8N ethanolic HCl (1.56 ml, 1.42 mmol). After evaporation to 20 ml, the hydrochloride of 4,6-dimethyl-3-(6',7'-dimethoxy-3',4'-dihydro-1H'-isoquinolin-2'-ylmethyl)-1H-indole 2-carboxylic acid precipitated out. The solid was separated and washed with water (10 ml). The product could be obtained with a yield of 61%. The grey solid had a melting point of 176–180° C.

Example 49

Synthesis of 4,6-dichloro-3-[4'-(3"-methoxyphenyl)-piperazin-1'-ylmethyl]-1H-indole 2-carboxylic acid dihydrochloride 4,6-Dichloro-3-[4'-(3"-methoxyphenyl)-piperazin-1'-ylmethyl]-1H-indole 2-carboxylic acid ethyl ester dihydrochloride (485 mg, 0.9 mmol) was dissolved in ethanol (60 ml) and combined with 1.7N KOH (16 ml, 27 mmol). After 16 hours' reaction time, the mixture was evaporated. The potassium salt of 4,6-dichloro-3-[4'-(3"-methoxyphenyl)-piperazin-1'-ylmethyl]-1H-indole 2-carboxylic acid was combined with ethyl acetate and 1.8N ethanolic HCl (3 ml, 5.4 mmol). The dihydrochloride formed was removed by suction filtration, the filtrate was further evaporated and the residue washed with water (10 ml). The product was obtained with a yield of 86%. The grey solid had a melting point of 177–182° C.

Example 50

Synthesis of 4,6-dichloro-3-(4'-carbamoyl-[1",4']bipiperidin-1'-ylmethyl)-1H-indole 2-carboxylic acid potassium salt 4,6-Dichloro-3-(4'-carbamoyl-[1",4']bipiperidin-1'-ylmethyl)-1H-indole 2-carboxylic acid ethyl ester (476 mg, 0.98 mmol) was dissolved in ethanol (90 ml), combined with 1.7N KOH (17.6 ml, 30 mmol) and stirred for 14 h. During evaporation of the batch, a colourless oil separated out, which became solid after a few minutes, was removed by suction filtration and washed with water. The potassium salt of 4,6-dichloro-3-(4'-carbamoyl-[1",4']bipiperidin-1'-ylmethyl)-1H-indole 2-carboxylic acid was obtained as a grey solid with a melting point of 193–196° C. in a yield of 70%. It was not possible to observe saponification of the amide function.

Example 51

Synthesis of 1-tert-butoxycarbonyl-4,6-dichloro-3-{[3'-N,N-dimethylaminomethyl)-4'-hydroxy-4-(3"-methoxyphenyl)-cyclohexylamino]-methyl}-indole 2-carboxylic acid ethyl ester 1-tert-Butoxycarbonyl-4,6-dichloro-3-(bromomethyl)-indole 2-carboxylic acid ethyl ester and 4-amino-2-(N,N-dimethylaminomethyl)-1-(3'-methoxyphenyl)-cyclohexan-1-ol were reacted in the presence of caesium carbonate in DMF. After a reaction time of 18 h at room temperature, the product was obtained in a yield of 55%. Purification was performed by flash chromatography.

Example 52

Synthesis of 4,6-dichloro-3-{[3'-N,N-dimethylaminomethyl)-4'-hydroxy-4'-(31"-methoxyphenyl)-cyclohexylamino]-methyl}-1-methyl-indole 2-carboxylic acid ethyl ester 4,6-Dichloro-3-formyl-1-methyl-indole 2-carboxylic acid ethyl ester and 4-amino-2-(N,N-dimethylaminomethyl)-1-(3'-methoxyphenyl)-cyclohexan-1-ol were converted into the imine in the presence of a 4 Å molecular sieve in diethyl ether. The imine was reduced to the amine after removal of the molecular sieve and solvent in ethanol with sodium cyanoborohydride. Purification was performed by chromatography. The product was obtained in a yield of 45%.

Example 53

Synthesis of 4,6-dichloro-3-[4'-(4"-chloro-3"-trifluoromethylphenyl)-4'-hydroxypiperidin-1'-ylmethyl]-1H-indole 2-carboxylic acid ethyl ester 4,6-Dichloro-3-formyl-1H-indole 2-carboxylic acid ethyl ester (286 mg, 1 mmol) was dissolved in THF (10 ml) and combined with 4'-(4"-chloro-3"-trifluoromethylphenyl)-4'-hydroxypiperidine (279 mg, 1 mmol). After 10 minutes, sodium triacetoxyborohydride (300 mg, 1.4 mmol) was added and stirring was then performed for 18 h. The reaction mixture was filtered, the residue combined with ethyl acetate (60 ml) and 5% NaHCO$_3$ (15 ml) and the mixture stirred for 15 minutes. The phases were separated and the organic phase extracted with water, dried and evaporated. A white solid with a melting point of 89–91° C. was obtained in a yield of 55%.

Example 54

Synthesis of 4,6-dimethyl-3-[4'-(4"-chloro-3"-trifluoromethylphenyl)-4'-hydroxypiperidin-1'-ylmethyl]-1H-indole 2-carboxylic acid ethyl ester 4,6-Dimethyl-3-formyl-1H-indole 2-carboxylic acid ethyl ester (490 mg, 2 mmol) and 4'-(4"-chloro-3"-trifluoromethylphenyl)-4-hydroxypiperidine (559 mg, 2 mmol) were dissolved in tetrahydrofuran (20 ml). After 10 minutes, NaBH(OAc)$_3$ (600 mg, 2.8 mmol) was added. After a reaction time of 19 h, the mixture was evaporated, the residue combined with diethyl ether (40 ml) and 0.5N HCl (40 ml, 20 mmol) and the mixture stirred for 1 h, wherein the hydrochloride of 4,6-dimethyl-3-[4'-(4"-chloro-3"-trifluoromethylphenyl)-4'-hydroxypiperidin-1'-ylmethyl]-1H-indole 2-carboxylic acid ethyl ester precipitated out as a solid. The solid was removed by suction filtration and then washed with diethyl ether and water. The crude product was combined with ethyl acetate (20 ml) and 5% NaHCO$_3$ (20 ml) and the mixture was stirred for 20 min. The phases were separated and the organic phase evaporated. A beige solid with a melting point of 77–81° C. was obtained in a yield of 60%.

Example 55

Synthesis of 4,6-dichloro-3-[4'-(4"-chloro-3"-trifluoromethylphenyl)-4'-hydroxypiperidin-1'-ylmethyl]-1H-indole 2-carboxylic acid hydrochloride 4,6-Dichloro-3-[4'-(4"-chloro-3"-trifluoromethylphenyl)-4'-hydroxypiperidin-1'-ylmethyl]-1H-indole 2-carboxylic acid ethyl ester (550 mg, 1 mmol) was resuspended in ethanol (30 ml), combined with 1.7N KOH (15 ml, 25.5 mmol) and stirred for 16 h. After evaporation of the reaction mixture, the potassium salt of 4,6-dichloro-3-[4'-(4"-chloro-3"-trifluoromethylphenyl)-4'-hydroxypiperidin-1'-ylmethyl]-1H-indole 2-carboxylic acid was extracted from the aqueous residue with ethyl acetate and then the organic phase was combined with 1.8N ethanolic hydrochloric acid (1.66 ml, 3 mmol). The solution was evaporated and the residue washed with water (2×10 ml). The product was obtained in a yield of 66% as a white crystalline product with a melting point of 206–209° C.

Example 56

Synthesis of 4,6-dimethyl-3-[4'-(4"-chloro-3"-trifluoromethylphenyl)-4'-hydroxypiperidin-1'-ylmethyl]-1H-indole 2-carboxylic acid hydrochloride To a solution of 4,6-dimethyl-3-[4'-(4"-chloro-3"-trifluoromethylphenyl)-4'-hydroxypiperidin-1'-ylmethyl]-1H-indole 2-carboxylic acid (332 mg, 0.65 mmol) in ethanol (20 ml) there was added 1.7N KOH (7.6 ml, 13 mmol) and the mixture was stirred for 16 hours. After evaporation of the solution, the potassium salt of 4,6-dimethyl-3-[4'-(4"-chloro-3"-trifluoromethylphenyl)-4'-hydroxypiperidin-1'-ylmethyl]-1H-indole 2-carboxylic acid was extracted and the extract combined with 1.8N ethanolic hydrochloric acid (2 ml, 3.6 mmol). On evaporation of the solution, 4,6-dimethyl-3-[4'-(4"-chloro-3"-trifluoromethylphenyl)-4'-hydroxypiperidin-1'-ylmethyl]-1H-indole 2-carboxylic acid hydrochloride precipitated out together with potassium chloride. Clean hydrochloride could be obtained with a yield of 89% by washing with water. The product was obtained as a grey solid with a melting point of 184–188° C.

Pharmacological Investigations

Analgesic Testing by Writhing Test in Mice

The in-depth investigation into the analgesic efficacy of the compounds according to the invention was performed using phenylquinone-induced writhing in mice, as described above. All the investigated compounds according to the invention exhibited a moderately strong to strong analgesic action.

The investigated compounds according to the invention exhibited an analgesic action. The results of selected writhing investigations are summarised in Table 1 below.

TABLE 1

| Compound No. | % inhibition of writhing reactions 10 mg/kg i.v. |
|---|---|
| 1 | 48 |
| 2 | 97 |
| 3 | 72 |
| 4 | 100 |

Compound nos. 1–4
1: 5-Chloro-3-{[3'-(N,N-dimethylaminomethyl)-4'-hydroxy-4'-(3''-methoxyphenyl)-cyclohexylamino]-methyl}-1H-indole 2-carboxylic acid ester,
2: 4,6-Dichloro-3-{[3'-(N,N-dimethylaminomethyl)-4'-hydroxy-4'-(3''-methoxyphenyl)-cyclohexylamino]-methyl}-1H-indole 2-carboxylic acid ethyl ester,
3: 4,6-Dichloro-3-{[3'-(N,N-dimethylaminomethyl)-4'-hydroxy-4'-(3''-methoxyphenyl)-cyclohexylamino]-methyl}-1H-indole 2-carboxylic acid,
4: 1-tert-Butoxycarbonyl-4,6-dichloro-3-{[3'-N,N-dimethylaminomethyl)-4'-hydroxy-4'-(3''-methoxyphenyl)-cyclohexylamino]-methyl}-indole 2-carboxylic acid ethyl ester.

The invention claimed is:
1. Substituted indoles of the formula I,

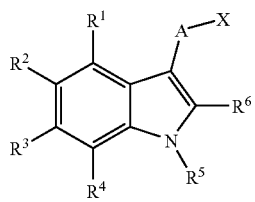

in which
R$^1$, R$^2$, R$^3$ and R$^4$, identical or different, denote a linear or branched, saturated or unsaturated aliphatic C$_{1-10}$ group or a saturated or unsaturated cycloaliphatic C$_{3-7}$ group, wherein each of the above-stated groups may optionally be joined together via an ether bridge, or hydrogen, a halogen or a hydroxy group,
R$^5$ denotes hydrogen, a linear or branched, saturated or unsaturated aliphatic C$_{1-10}$ group, a saturated or unsaturated cycloaliphatic C$_{3-7}$ group, an aryl or heteroaryl group, wherein the aryl or heteroaryl group may be optionally joined together via a C$_{1-6}$ alkylene group, a substituted sulfonyl group or a group of the formula —COR$^7$, wherein R$^7$ has the meaning stated hereinafter,
R$^6$ denotes a group of the formula —COR$^7$, a thiol group, a hydroxy group, a halogen, a cyano group, a nitro group or a group of the formula SO$_2$CH$_3$, SO$_2$CF$_3$ or —CF$_3$, wherein the group R$^7$ has the meaning stated hereinafter,
R$^7$ denotes the group OR$^8$, SR$^8$, or NR$^8$R$^9$, wherein the groups R$^8$ and R$^9$ have the meaning stated hereinafter,
R$^8$ and R$^9$, identical or different, denote hydrogen, a linear or branched, saturated or unsaturated aliphatic C$_{1-10}$ group, a saturated or unsaturated cycloaliphatic C$_{3-7}$ group, an aryl- or heteroaryl group or an aryl or heteroaryl group attached via a C$_{1-6}$ alkylene group, A denotes a bridge with one of the following formulae:
—(CH$_2$)$_{1-2}$—, —CH=CH—, —(CH$_2$)$_n$COO—, —(CH$_2$)$_n$CONH—, —(CH$_2$)$_n$O(CH$_2$)$_p$CO—, —(CH$_2$)$_n$O—, —(CH$_2$)$_n$NR$^{1'}$—, in which n denotes 0, 1, 2 or 3, and p denotes 0 or 1, R$^{1'}$ has the meaning stated hereinafter and the bond to the group X is always stated last and only a nitrogenous residue may be joined to the bridge of the formula —CH$_2$— via the nitrogen,
and X denotes one of the following residues of the formulae X$^{1-6}$, X$^{11-12}$, X$^{15-16}$ and X$^{19}$, in which the unoccupied bond line symbolises the bond to the bridge A and X$^1$
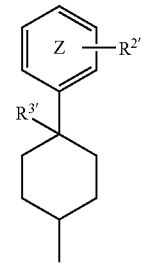

X$^2$
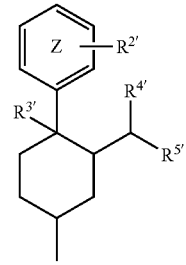

X$^3$
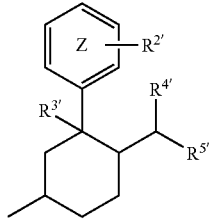

X$^4$
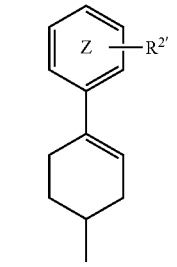

X$^5$
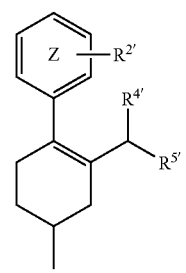

-continued

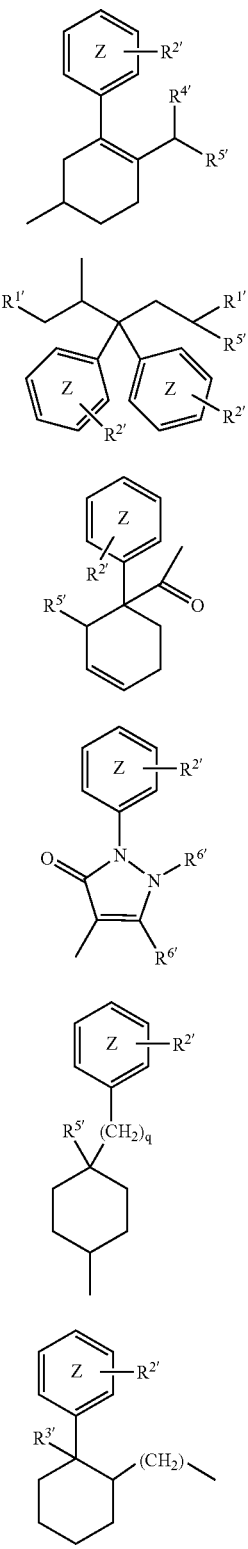

R[1'] denotes hydrogen, a linear or branched, saturated or unsaturated aliphatic $C_{1-10}$ group, a saturated or unsaturated cycloaliphatic $C_{3-7}$ group, an aryl or heteroaryl, group R[2'] denotes a linear or branched, saturated or unsaturated aliphatic $C_{1-10}$ group, a saturated or unsaturated cycloaliphatic $C_{3-7}$ group or an aryl or heteroaryl group, wherein all the above-stated groups may optionally be joined via an ether, thioether or $SO_2$ bridge, or hydrogen, a halogen, a hydroxy, thiol, cyano or nitro group or a group of the formula $-CH_2F$, $-CHF_2$, $-CF_3$ or $NR^{1'}{}_2$, wherein the two groups R[1'] are identical or different and have the above-stated meaning, R[3'] denotes a linear or branched, saturated or unsaturated aliphatic $C_{1-10}$ group, a saturated or unsaturated cycloaliphatic $C_{3-7}$ group, an aryl or heteroaryl group, wherein all the above-stated groups may optionally be joined via an ether or an ester bridge, hydrogen, a halogen, a hydroxy group, R[4'] denotes hydrogen, an aryl or heteroaryl group, wherein the aryl or heteroaryl group may comprise at least one substituent R[2'] with the above meaning, with the exception of hydrogen, R[5'] denotes a residue of the formula $-NR^{6'}{}_2$, wherein the two groups R[6'] may be identical or different and have the meaning stated hereinafter or may form a 3–7-membered ring together with the nitrogen atom connecting them as a ring member, which ring may optionally contain at least one oxygen and/or at least one further nitrogen as a ring atom, wherein the nitrogen may comprise a substituent R[10'] with the meaning stated hereinafter, R[6'] denotes a linear or branched, saturated or unsaturated aliphatic $C_{1-6}$ group, a saturated or unsaturated cycloaliphatic $C_{3-7}$ group, an aryl or heteroaryl group, R[10'] denotes hydrogen, a linear or branched, saturated or unsaturated aliphatic $C_{1-10}$ group, an aryl or heteroaryl group and Z denotes that there is no heteroatom present as a ring atom, and q denotes 0, 1, 2 or 3, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

2. Substituted indoles according to claim 1, characterised in that $R^2$ denotes a linear or branched, saturated or unsaturated aliphatic $C_{1-3}$ group or a halogen and $R^1$, $R^3$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

3. Substituted indoles according to claim 1, characterised in that $R^3$ denotes a linear or branched, saturated or unsaturated aliphatic $C_{1-3}$ group or a halogen and $R^1$, $R^2$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

4. Substituted indoles according to claim 1, characterised in that $R^2$ and $R^3$, identical or different, denote a linear or branched, saturated or unsaturated aliphatic $C_{1-3}$ group or a halogen and $R^1$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

5. Substituted indoles according to claim 1, characterised in that $R^1$ and $R^3$, identical or different, denote a linear or branched, saturated or unsaturated aliphatic $C_{1-3}$ group or a halogen and $R^2$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

6. Substituted indoles according to claim 1, characterised in that $R^2$ denotes a methyl group or a chlorine and $R^1$, $R^3$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

7. Substituted indoles according to claim 1, characterised in that $R^3$ denotes a methyl group or a chlorine and $R^1$, $R^2$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

8. Substituted indoles according to claim 1, characterised in that $R^2$ and $R^3$ in each case denote a methyl group or a chlorine and $R^1$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

9. Substituted indoles according to claim 1, characterised in that $R^1$ and $R^3$ in each case denote a methyl group or a chlorine and $R^2$ and $R^4$ in each case denote hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

10. Substituted indoles according to claim 1, characterised in that $R^5$ denotes hydrogen, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

11. Substituted indoles according to claim 1, characterised in that $R^6$ denotes a group of the formula $COR^7$, wherein $R^7$ denotes the group $OR^8$ and the residue $R^8$ denotes hydrogen or a linear or branched, saturated or unsaturated aliphatic $C_{1-3}$ group, preferably a methyl or ethyl group, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

12. Substituted indoles according to claim 1, characterised in that $R^7$ denotes the group $OR^8$ or $SR^8$, wherein the group $R^8$ has the meaning according to claim 1, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

13. Substituted indoles according to claim 1, characterised in that A denotes a bridge with one of the following formulae: —$CH_2$—, —$CH_2NR^{1''}$—, in which $R^{1''}$ denotes hydrogen or a linear or branched, saturated or unsaturated aliphatic $C_{1-3}$ group, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

14. Substituted indoles according to claim 1, characterised in that X denotes a group of the following formula,

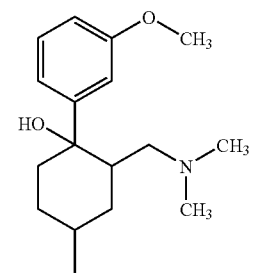

optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

15. A substituted indole according to claim 1, selected from the group consisting of:

5-Methyl-3-{[3'-(N,N-dimethylaminomethyl)-4'-hydroxy-4'-(3''-methoxyphenyl)-cyclohexylamino]-methyl}-1H-indole 2-carboxylic acid methyl ester, 4,6-Dimethyl-3-{[3'-(N,N-dimethylaminomethyl)-4-hydroxy-4'-(3''-methoxyphenyl)-cyclohexylamino]-methyl}-1H-indole 2-carboxylic acid ethyl ester, 5-Chloro-3-{[3'-(N,N-dimethylaminomethyl)-4'-hydroxy-4'-(3''-methoxyphenyl)-cyclohexylamino]-methyl}-1H-indole 2-carboxylic acid ethyl ester, 4,6-Dichloro-3-{[3'-(N,N-dimethylaminomethyl)-4'-hydroxy-4'-(3''-methoxyphenyl)-cyclohexylamino]-methyl}-1H-indole 2-carboxylic acid ethyl ester, 4,6-Dimethyl-3-{[3'-(N,N-dimethylaminomethyl)-4'-hydroxy-4'-(3''-methoxyphenyl)-cyclohexyl-(N-methylamino)]-methyl}-1H-indole 2-carboxylic acid ethyl ester 4,6-Dichloro-3-{[3'-(N,N-dimethylaminomethyl)-4'-hydroxy-4'-{3''-methoxyphenyl)-cyclohexyl-(N-methylamino)]-methyl}-1H-indole 2-carboxylic acid ethyl ester, 5-Chloro-3-{[3'-(N,N-dimethylaminomethyl)-4'-hydroxy-4'-(3''-methoxyphenyl)-cyclohexyl-(N-methylamino)]-methyl}-1H-indole 2-carboxylic acid ethyl ester, 5-Methyl-3-{[3'-(N,N-dimethylaminomethyl)-4'-hydroxy-4'-(3''-methoxyphenyl)-cyclohexylamino]-methyl}-1H-indole 2-carboxylic acid, 5-Chloro-3-{[3'-(N,N-dimethylaminomethyl)-4'-hydroxy-4'-(3''-methoxyphenyl)-cyclohexylamino]-methyl}-1H-indole 2-carboxylic acid, 4,6-Dimethyl-3-{[3'-(N,N-dimethylaminomethyl)-4'-hydroxy-4'-(3''-methoxyphenyl)-cyclohexylamino]-methyl}-1H-indole 2-carboxylic acid, 4,6-Dichloro-3-{[3'-(N,N-dimethylaminomethyl)-4'-hydroxy-4'-(3''-methoxyphenyl)-cyclohexylamino]-methyl}-1H-indole 2-carboxylic acid, 4,6-Dichloro-3-{[4'-hydroxy-4'-(3''-methoxyphenyl)-cyclohexylamino]-methyl}-1H-indole 2-carboxylic acid ethyl ester, 4,6-Dichloro-3-({[4'-hydroxy-4'-(3''-methoxyphenyl)-cyclohexyl]-(N-methylamino)}-methyl)-1H-indole 2-carboxylic acid ethyl ester 4,6-Dichloro-3-({[2'-hydroxy-2'-(3''-methoxyphenyl)-cyclohexylmethyl]-amino}-methyl)-1H-indole 2-carboxylic acid ethyl ester, 5-Chloro-3-({[2'-hydroxy-2'-(3''-methoxyphenyl)-cyclohexylmethyl]-amino}-methyl)-1H-indole 2-carboxylic acid ethyl ester, 4,6-Dimethyl-3-({[2'-hydroxy-2'-(3''-methoxyphenyl)-cyclohexylmethyl]-amino}-methyl)-1H-indole 2-carboxylic acid ethyl ester, 5-Methyl-3-({[2'-hydroxy-2'-(3''-methoxyphenyl)-cyclohexylmethyl]-amino}-methyl)-1H-indole 2-carboxylic acid ethyl ester, 4,6-Dichloro-3-({[2'-hydroxy-2'-(3''-hydroxyphenyl)-cyclohexylmethyl]-amino}-methyl)-1H-indole 2-carboxylic acid ethyl ester, 5-Chloro-3-({[2'-hydroxy-2'-(3''-hydroxyphenyl)-cyclohexylmethyl]-amino}-methyl)-1H-indole 2-carboxylic acid ethyl ester, 4,6-Dimethyl-3-({[2'-hydroxy-2'-(3''-hydroxyphenyl)-cyclohexylmethyl]-amino}-methyl)-1H-indole 2-carboxylic acid ethyl ester, 5-Methyl-3-({[2'-hydroxy-2'-(3''-hydroxyphenyl)-cyclohexylmethyl]-amino}-methyl)-1H-indole 2-carboxylic acid ethyl ester, 4,6-Dichloro-3-({[2'-hydroxy-2'-(3''-methoxyphenyl)-cyclohexylmethyl]-amino}-methyl)-1H-indole 2-carboxylic acid, 5-Chloro-3-({[2'-hydroxy-2'-(3''-methoxyphenyl)-cyclohexylmethyl]-amino}-methyl)-1H-indole 2-carboxylic acid, 4,6-Dimethyl-3-({[2'-hydroxy-2'-(3''-methoxyphenyl)-cyclohexylmethyl]-amino}-methyl)-1H-indole 2-carboxylic acid, 5-Methyl-3-({[2'-hydroxy-2'-(3''-methoxyphenyl)-cyclohexylmethyl]-amino}-methyl)-1H-indole 2-carboxylic acid, 4,6-Dichloro-3-({[2'-hydroxy-2'-(3''-hydroxyphenyl)-cyclohexylmethyl]-amino}-methyl)-1H-indole 2-carboxylic acid, 5-Chloro-3-({[2'-hydroxy-2'-(3''-hydroxyphenyl)-cyclohexylmethyl]-amino}-methyl)-1H-indole 2-carboxylic acid, 4,6-Dichloro-3-[(1',5'-dimethyl-3'-oxo-2'-phenyl-2',3'-dihydro-1'H-pyrazol-4'-ylamino)-methyl]-1H-indole 2-carboxylic acid ethyl ester, 4,6-Dimethyl-3-[(1',5'-dimethyl-3'-oxo-2'-phenyl-2',3'-dihydro-1'H-pyrazol-4'-ylamino)-methyl]-1H-indole 2-carboxylic acid ethyl ester, 4,6-Dichloro-3-{[(4'-benzyl-4'-(N,N-dimethylamino)-cyclohexyl)-(N-propylamino)]-methyl}-1H-indole 2-carboxylic acid ethyl ester, 4,6-Dichloro-3-[(1',5'-dimethyl-3'-oxo-2'-phenyl-2',3'-dihydro-1'H-pyrazol-4'-ylamino)-methyl]-1H-indole 2-carboxylic acid, 1-tert-Butoxycarbonyl-4,6-dichloro-3-{[3'-N,N-dimethylaminomethyl)-4'-hydroxy-4'-(3''-methoxyphenyl)-cyclohexylamino]-methyl}-indole 2-carboxylic acid ethyl ester, 4,6-Dichloro-3-{[3'-(N,N-dimethylaminomethyl)-4'-hydroxy-4'-(3''-methoxyphenyl)-cyclohexylamino]-methyl}-1H-methyl-indole 2-carboxylic acid ethyl ester, 4,6-Dichloro-3-{[3'-(N,N-dimethylaminomethyl)-4'-hydroxy-4'-(3''-methoxyphenyl)-cyclohexylamino]-methyl}-1-benzyl-indole 2-carboxylic acid ethyl ester, and 5-Chloro-3-{[3'-(N,N-dimethylaminomethyl)-4'-hydroxy-4'-(3''-methoxyphenyl)-cyclohexylamino]-methyl}-1-benzyl-indole 2-carboxylic acid ethyl ester, optionally in the form of the racemates thereof, the pure stereoisomers thereof, or in the form of mixtures of the stereoisomers, in any desired mixing ratio or in each case in the form of the acids or bases thereof or in the form of the salts thereof, or in the form of the solvates thereof.

16. A process for the production of substituted indoles according to claim 1, in which A) an indole of the formula Y—$R^x$ is optionally derivatised, in which $R^x$ denotes hydrogen or a group of the formulae $(CH_2)_n COOR$, $(CH_2)_n OH$ or $(CH_2)_n NR^{1'}H$, in which n denotes 0, 1, 2 or 3 and $R^{1'}$ has the meaning according to claim 1 and R denotes hydrogen or an alkyl group, preferably a methyl or ethyl group, and Y denotes a group of the formula Y, in which the unoccupied bond line symbolises the bond to the residue $R^x$

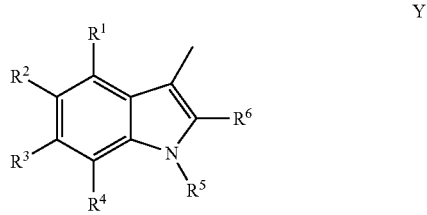

and in which $R^1$, $R^2$, $R^3$, $R^4$, $R^5$ and $R^6$ have the above-stated meaning, in that a) an indole of the formula Y—H is reacted with an N,N-disubstituted formamide, preferably N-methyl-N-phenylformamide, in the presence of phosphorus oxychloride in a suitable solvent, preferably 1,2-dichloroethane, to yield the corresponding aldehyde of the formula Y—CHO, b) an aldehyde of the formula Y—CHO according to step a) is reacted with the assistance of reducing agents, preferably sodium cyanoborohydride or $NaBH_2S_3$, in a suitable solvent, optionally in the presence of a buffer and with cooling to yield the corresponding alcohol of the formula Y—$CH_2$—OH, c) an alcohol of the formula Y—$(CH_2)_n$—OH according to step b) or D) is reacted with a brominating agent, preferably $PBr_3$ or $Ph_3PBr_2$ to yield the corresponding bromide of the formula Y—$(CH_2)_n$—Br, d) an ester of the formula Y—$(CH_2)_n$—COOR, in which R denotes an alkyl group, preferably a methyl or ethyl group, is saponified in the presence of a base, preferably sodium or potassium hydroxide, in a suitable solvent, preferably an alcohol/water mixture, particularly preferably in a methanol/ or ethanol/water mixture, to yield the corresponding carboxylic acid of the formula Y—$(CH_2)_n$—COOH and is then worked up and the product is optionally purified, B) a compound of the formula $X^1$—R', in which $X^1$ has the above-stated meaning and R' denotes a functional group, is optionally produced in that a) 1,4-cyclohexanedione monoethylene ketal, 4-aminocyclohexan-1-one ethylene ketal or 4-oxocyclohexanecarboxylic acid is reacted with magnesium and a brominated or chlorinated, optionally substituted aromatic or heteroaromatic compound in a suitable solvent, preferably dry diethyl ether, at elevated temperature to yield the corresponding coupling product and then the ketal is optionally cleaved by reaction with hydrochloric acid in a suitable solvent, preferably tetrahydrofuran and is worked up, optionally followed by purification of the product of the formula $X^{1a}$=O, $X^{1a}$—NHR$^{1'}$ or $X^{1a}$—CO$_2$H, in which $X^{1a}$ denotes a residue of the formula $X^{1a}$ and R$^{1'}$, R$^{2'}$ and Z have the above-stated meaning and the unoccupied bond line symbolises the bond to the respective residue =O, —NHR$^{1'}$ or —CO$_2$H,

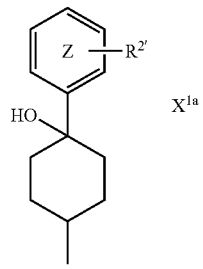

b) a ketone of the formula $X^{1a}$=O is optionally reacted in the presence of a suitable reducing agent, preferably sodium borohydride, in a suitable solvent, preferably methanol, to yield the corresponding alcohol of the formula $X^{1a}$—OH, is worked up and the product is optionally purified, c) a ketone of the formula $X^{1a}$=O is optionally reacted under protective gas, preferably nitrogen, in a suitable solvent, preferably tetrahydrofuran, firstly with ammonium trifluoroacetate and then with glacial acetic acid and sodium triacetoxyborohydride, to yield the corresponding amine of the formula $X^{1a}$—NH$_2$, is worked up and the product is optionally purified, d) a carboxylic acid of the formula $X^{1a}$—CO$_2$H is optionally activated by reaction with dicyclohexylcarbodiimide or by conversion into the carboxylic acid chloride or a mixed anhydride, is reacted with diazomethane in a suitable solvent, preferably ether, and then treated with water, worked up and the product of the formula $X^{1a}$—CO—CH$_2$—OH is optionally purified, e) the hydroxy group in position 4 of the cyclohexane ring in the group $X^{1a}$ is optionally converted into hydrogen, a halogen, an ether, ester, aryl or heteroaryl group or into an aliphatic or cycloaliphatic group, in that α) in order to introduce an ether group, a compound from one of steps a)–d) is reacted with an aliphatic or cycloaliphatic group in the presence of a suitable catalyst in a suitable solvent, preferably in the presence of sodium hydride in dimethylformamide or in the presence of potassium hydroxide in dimethyl sulfoxide, or with an alkylating agent in a suitable solvent, preferably with a diazo compound in diethyl ether, or with an aryl or heteroaryl compound in the presence of diethylazo dicarboxylate and triphenylphosphine, β) in order to introduce a halogen, a compound from one of steps a)-d) is reacted with a halogenating agent in a suitable solvent, preferably with POCl$_3$ in dimethylformamide, with PPh$_3$/Cl$_2$, with PPh$_3$/Br$_2$, with triphenylphosphine/n-chlorosuccinimide or with HCl/ZnCl$_2$, χ) in order to introduce a hydrogen, a compound from step β) is reacted with hydrogen in the presence of a suitable catalyst, preferably palladium/carbon, in a suitable solvent, δ) in order to introduce an aliphatic or cycloaliphatic group or an aryl or heteroaryl group, a compound from step β) is reacted with an aliphatic or cycloaliphatic boronic acid or a boronic acid ester or an aryl or heteroaryl borodihydroxide compound in the presence of palladium(II) acetate and potassium carbonate in a suitable solvent, preferably a dimethylformamide/water mixture, or ε) in order to introduce an ester group, a compound from one of steps a)–d) is reacted with a corresponding carboxylic acid chloride in the presence of a suitable catalyst in a suitable solvent and is then worked up, optionally followed by purification of the compound formed of the formula $X^1$—R', in which $X^1$ denotes the formula $X^1$

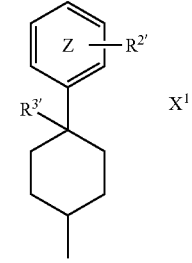

and R', R$^{2'}$ and R$^{3'}$ have the above-stated meaning,

C) a compound of the formula X—R', in which X has the above-stated meaning and R' denotes a functional group, is optionally derivatised in that a) a ketone of the formula X=O is reacted 1) with methoxymethyl triphenylphosphinium chloride under protective gas in a suitable solvent, preferably in dimethylformamide, in the presence of sodium hydride and then with hydrochloric acid or 2) with Me$_3$S$^+$BF$_4^-$ to yield the corresponding aldehyde X—CHO extended by one carbon atom, b) an aldehyde of the formula X—CHO according to a) is reacted with a reducing agent, preferably sodium borohydride, in a suitable solvent, preferably an ethanol/water mixture, to yield the corresponding alcohol X—CH$_2$—OH, c) an alcohol X—CH$_2$—OH according to b) or of the formula X—OH is reacted with a brominating agent, preferably triphenylphosphine dibromide, in a suitable solvent, preferably acetonitrile, to yield the corresponding bromide of the formula X—CH$_2$—Br or X—Br, d) a bromide of the formula X—CH$_2$—Br according to c) is reacted with a phosphine of the formula PR"$_3$, in which R" denotes an organic group, preferably a phenyl group, in a suitable solvent, preferably toluene, ether, tetrahydrofuran or acetone, with cooling and under protective gas to yield the corresponding phosphonium salt R"$_3$P$^+$—CHX$^-$, e) a bromide of the formula X—CH$_2$—Br according to c) is reacted with a phosphite of the formula HP(O)(OR''')$_2$, in which R''' denotes an organic group, at elevated temperature, preferably 200° C., to yield the corresponding phosphonate (R'''0)$_2$P(O)—CH$_2$—X and is then worked up and the product is optionally purified, D) a compound of the formula Y—R$^x$ or the derivative thereof from step A), in which Y has the above-stated meaning, is reacted with a compound of the formula X$^1$—R' or the derivative thereof from step B) or a compound of the formula X—R' or the derivative thereof from step C), in which X and R' have the above-stated meaning, in that a) a carboxylic acid of the formula Y—(CH$_2$)$_n$—COOH is reacted with an amine of the formula X—NH$_2$ in the presence of a suitable condensing agent, preferably dicyclohexyl carbodiimide, 1-hydroxybenzotriazole and N-methylmorphine, in a suitable solvent, preferably dimethylformamide, with formation of an amide bridge, b) a carboxylic acid of the formula Y—(CH$_2$)$_n$—COOH is reacted with an alcohol of the formula X—OH in the presence of a suitable condensing agent in a suitable solvent with formation of an ester bridge, the reaction preferably taking place in the presence of methylimidazole and 1-(mesitylene-2'-sulfonyl)-3-nitro-1,2,4-triazole in tetrahydrofuran or in the presence of dicyclohexylcarbodiimide, 1-hydroxybenzotriazole and N-methylmorphine in dimethylformamide, c) a bromide of the formula Y—(CH$_2$)$_n$—Br is reacted with a compound of the formula X—CO(CH$_2$)$_p$—OH, in which p has the above-stated meaning, under protective gas in the presence of a suitable catalyst, preferably sodium hydride or potassium tert-butylate, in a suitable solvent, preferably dimethylformamide, with formation of a bridge of the formula —CO(CH$_2$)$_p$—O—(CH$_2$)$_n$—, d) an alcohol of the formula Y—(CH$_2$)$_n$—OH is reacted with a bromide of the formula X—Br under protective gas in the presence of a suitable condensing agent, preferably sodium hydride or potassium tert-butylate, in a suitable solvent, preferably dimethylformamide, with formation of an ether bridge, e) a bromide of the formula Y—(CH$_2$)$_n$—Br is reacted with an alcohol of the formula X—OH under protective gas in the presence of a suitable condensing agent, preferably sodium hydride or potassium tert-butylate, in a suitable solvent, preferably dimethylformamide, with formation of an ether bridge, f) an amine of the formula Y—(CH$_2$)$_n$—NHR$^{1'}$ is reacted with a bromide of the formula X—Br in the presence of a suitable catalyst, preferably caesium carbonate, in a suitable solvent, preferably dimethylformamide, with formation of an amino bridge, g) a bromide of the formula Y—(CH$_2$)$_n$—Br is reacted with an amine of the formula X—NHR$^{1'}$ in the presence of a suitable catalyst, preferably caesium carbonate, in a suitable solvent, preferably dimethylformamide, with formation of an amino bridge, h) an aldehyde of the formula Y—CHO is reacted with an amine of the formula X—NHR$^{1'}$ in the presence of a suitable reducing agent, preferably sodium cyanoborohydride and sodium triacetoxyborohydride, in a suitable solvent, preferably a mixture of tetrahydrofuran and 1,2-dichloroethane, with formation of a —CH$_2$—NR$^{1'}$ bridge, i) an aldehyde of the formula Y—CHO is reacted with a phosphonium salt R"$_3$P$^+$—CHX$^-$, in which R" has the above-stated meaning, under protective gas in the presence of suitable catalysts in a suitable solvent, preferably in the presence of sodium methanolate in a mixture of hexane, diethyl ether and/or diisopropyl ether or in the presence of sodium hydride, potassium tert-butylate or a lithium amide in dimethylformamide or dimethyl sulfoxide, with formation of a —CH=CH— bridge or j) an aldehyde of the formula Y—CHO is reacted with a phosphonate of the formula (R'''O)$_2$P(O)—CH$_2$—X, in which R''' has the above-stated meaning, under protective gas in the presence of suitable catalysts, preferably sodium methanolate, sodium hydroxide, potassium hydroxide, sodium hydride, potassium tert-butylate or a lithium amide, in a suitable solvent, preferably dimethylformamide, dimethyl sulfoxide, diethyl ether, tetrahydrofuran, with formation of a —CH=CH— bridge, k) the —CH=CH— bridge from step i) or j) is optionally hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. with formation of a —CH$_2$—CH$_2$— bridge, l) an aldehyde of the formula Y—CHO is reacted with a compound of the formula X—H, wherein X denotes a nitrogenous group, in which the hydrogen is attached to the nitrogen, in the presence of a suitable catalyst, preferably sodium cyanoborohydride or sodium triacetoxyborohydride, in a suitable solvent, preferably 1,2-dichloroethane, with formation of a —CH$_2$— bridge and is then worked up and the product is optionally purified, E) an indole 2-carboxylic acid ester of the formula Y—A—X, in which Y, A and X have the above-stated meaning, wherein R$^6$ in Y denotes a group of the formula COR$^7$, in which R$^7$ denotes the group OR$^8$ and R$^8$ has the above-stated meaning with the exception of hydrogen, is optionally saponified in the presence of a base, preferably potassium or sodium hydroxide, in a suitable solvent, preferably an alcohol/water mixture, particularly preferably in a methanol/ or ethanol/water mixture and then worked up, followed optionally by purification of the indole 2-carboxylic acid of the formula Y—A—X, in which R$^6$ in Y denotes a group of the formula COR$^7$, in which R$^7$ denotes the group OR$^8$ and R$^8$ denotes hydrogen.

17. A pharmaceutical preparation containing at least one substituted indole compound according to claim 1, optionally in the form of the racemate thereof, the pure stereoisomer thereof, or in the form of mixtures of the stereoisomers, in any desired mixing ratio or in each case in the form of the acid or base thereof or in the form of the salt thereof, or in the form of the solvate thereof.

18. A method of combating pain comprising administering to a patient in need thereof a pain relieving amount of a pharmaceutical preparation comprising at least one compound according to claim 1 and physiologically acceptable auxiliary substances.

19. The method of claim 18 where the pain is chronic pain.

20. The method of claim 18 where the pain is-neuropathic pain.

21. A method of treating migraine comprising administering to a patient in need thereof a therapeutically effective amount of a pharmaceutical preparation comprising at least one compound according to claim 1 and physiologically acceptable auxiliary substances.

22. A method of inducing anaesthesia comprising administering to a patient in need thereof a therapeutically effective amount of a pharmaceutical preparation comprising at least one compound according to claim 1 and physiologically acceptable auxiliary substances.

23. A pharmaceutical preparation comprising at least one compound of claim 2 and physiologically acceptable auxiliary substances.

24. A pharmaceutical preparation comprising at least one compound of claim 3 and physiologically acceptable auxiliary substances.

25. A pharmaceutical preparation comprising at least one compound of claim 4 and physiologically acceptable auxiliary substances.

26. A pharmaceutical preparation comprising at least one compound of claim 5 and physiologically acceptable auxiliary substances.

27. A pharmaceutical preparation comprising at least one compound of claim 6 and physiologically acceptable auxiliary substances.

28. A pharmaceutical preparation comprising at least one compound of claim 7 and physiologically acceptable auxiliary substances.

29. A pharmaceutical preparation comprising at least one compound of claim 8 and physiologically acceptable auxiliary substances.

30. A pharmaceutical preparation comprising at least one compound of claim 9 and physiologically acceptable auxiliary substances.

31. A pharmaceutical preparation comprising at least one compound of claim 10 and physiologically acceptable auxiliary substances.

32. A pharmaceutical preparation comprising at least one compound of claim 11 and physiologically acceptable auxiliary substances.

33. A pharmaceutical preparation comprising at least one compound of claim 12 and physiologically acceptable auxiliary substances.

34. A pharmaceutical preparation comprising at least one compound of claim 13 and physiologically acceptable auxiliary substances.

35. A pharmaceutical preparation comprising at least one compound of claim 14 and physiologically acceptable auxiliary substances.

36. A pharmaceutical preparation comprising at least one compound of claim 15 and physiologically acceptable auxiliary substances.

37. Substituted indoles of claim 1 in the form of enantiomers or diastereomers, mixtures of enantiomers or diastereomers in any desired mixing ratio, physiologically acceptable salts thereof, or hydrates thereof.

38. Substituted indoles of claim 2 in the form of enantiomers or diastereomers, mixtures of enantiomers or diastereomers in any desired mixing ratio, physiologically acceptable salts thereof, or hydrates thereof.

39. Substituted indoles of claim 3 in the form of enantiomers or diastereomers, mixtures of enantiomers or diastereomers in any desired mixing ratio, physiologically acceptable salts thereof, or hydrates thereof.

40. Substituted indoles of claim 4 in the form of enantiomers or diastereomers, mixtures of enantiomers or diastereomers in any desired mixing ratio, physiologically acceptable salts thereof, or hydrates thereof.

41. Substituted indoles of claim 5 in the form of enantiomers or diastereomers, mixtures of enantiomers or diastereomers in any desired mixing ratio, physiologically acceptable salts thereof, or hydrates thereof.

42. Substituted indoles of claim 6 in the form of enantiomers or diastereomers, mixtures of enantiomers or diastereomers in any desired mixing ratio, physiologically acceptable salts thereof, or hydrates thereof.

43. Substituted indoles of claim 7 in the form of enantiomers or diastereomers, mixtures of enantiomers or diastereomers in any desired mixing ratio, physiologically acceptable salts thereof, or hydrates thereof.

44. Substituted indoles of claim 8 in the form of enantiomers or diastereomers, mixtures of enantiomers or diastereomers in any desired mixing ratio, physiologically acceptable salts thereof, or hydrates thereof.

45. Substituted indoles of claim 9 in the form of enantiomers or diastereomers, mixtures of enantiomers or diastereomers in any desired mixing ratio, physiologically acceptable salts thereof, or hydrates thereof.

46. Substituted indoles of claim 10 in the form of enantiomers or diastereomers, mixtures of enantiomers or diastereomers in any desired mixing ratio, physiologically acceptable salts thereof, or hydrates thereof.

47. Substituted indoles of claim 11 in the form of enantiomers or diastereomers, mixtures of enantiomers or diastereomers in any desired mixing ratio, physiologically acceptable salts thereof, or hydrates thereof.

48. Substituted indoles of claim 12 in the form of enantiomers or diastereomers, mixtures of enantiomers or diastereomers in any desired mixing ratio, physiologically acceptable salts thereof, or hydrates thereof.

49. Substituted indoles of claim 13 in the form of enantiomers or diastereomers, mixtures of enantiomers or diastereomers in any desired mixing ratio, physiologically acceptable salts thereof, or hydrates thereof.

50. Substituted indoles of claim 14 in the form of enantiomers or diastereomers, mixtures of enantiomers or diastereomers in any desired mixing ratio, physiologically acceptable salts thereof, or hydrates thereof.

51. Substituted indoles of claim 15 in the form of enantiomers or diastereomers, mixtures of enantiomers or diastereomers in any desired mixing ratio, physiologically acceptable salts thereof, or hydrates thereof.

52. Substituted indoles of claim 17 in the form of enantiomers or diastereomers, mixtures of enantiomers or diastereomers in any desired mixing ratio, physiologically acceptable salts thereof, or hydrates thereof.

53. A pharmaceutical preparation comprising at least one compound of claim 1 and physiologically acceptable auxiliary substances.

* * * * *